(12) United States Patent
Nonn et al.

(10) Patent No.: US 12,034,904 B2
(45) Date of Patent: Jul. 9, 2024

(54) ENDOSCOPIC IMAGING SYSTEMS FOR GENERATING THREE DIMENSIONAL IMAGES, AND ASSOCIATED SYSTEMS AND METHODS

(71) Applicant: Proprio, Inc., Seattle, WA (US)

(72) Inventors: Thomas Ivan Nonn, Kenmore, WA (US); Adam Gabriel Jones, Seattle, WA (US); James Andrew Youngquist, Seattle, WA (US)

(73) Assignee: Proprio, Inc., Seattle, WA (US)

( * ) Notice: Subject to any disclaimer, the term of this patent is extended or adjusted under 35 U.S.C. 154(b) by 0 days.

(21) Appl. No.: 17/482,225

(22) Filed: Sep. 22, 2021

(65) Prior Publication Data

US 2022/0094901 A1    Mar. 24, 2022

Related U.S. Application Data

(60) Provisional application No. 63/082,027, filed on Sep. 23, 2020.

(51) Int. Cl.
*H04N 13/117* (2018.01)
*A61B 1/00* (2006.01)
(Continued)

(52) U.S. Cl.
CPC ....... *H04N 13/117* (2018.05); *A61B 1/00193* (2013.01); *A61B 1/05* (2013.01);
(Continued)

(58) Field of Classification Search
CPC .... H04N 13/117; H04N 13/167; H04N 13/25; H04N 13/254; H04N 2213/001;
(Continued)

(56) References Cited

U.S. PATENT DOCUMENTS 6,675,040 B1    1/2004 Cosman
9,916,691 B2    3/2018 Takano et al.
(Continued)

FOREIGN PATENT DOCUMENTS

EP    1924197 B1    10/2017
EP    3197382 A4    6/2018
(Continued)

OTHER PUBLICATIONS

International Search Report and Written Opinion received in Application No. PCT/US21/51569, dated Jan. 19, 2022, 22 pages.

*Primary Examiner* — Michael Lee
(74) *Attorney, Agent, or Firm* — Perkins Coie LLP

(57) ABSTRACT

Endoscopic imaging systems are disclosed herein. In some embodiments, an endoscopic imaging system can include an endoscope having a distal tip with a distal face configured to face a scene, such as a portion of a body cavity of a patient. The endoscope can further include first cameras for capturing first image data of the scene, a projector for projecting a light pattern into the scene, and second cameras for capturing second image data of the scene including the light pattern. A processor can be communicatively coupled to the first and second cameras for receiving the first and second image data. The processor can process the first and second image data to generate an image of the scene at the perspective of a virtual camera, and can vary the perspective, the aperture, the focus plane, and/or another parameter of the virtual camera without requiring the endoscope to be physically moved.

20 Claims, 13 Drawing Sheets

(51) Int. Cl.
*A61B 1/05* (2006.01)
*H04N 13/167* (2018.01)
*H04N 13/25* (2018.01)
*H04N 13/254* (2018.01)

(52) U.S. Cl.
CPC ........... *H04N 13/167* (2018.05); *H04N 13/25* (2018.05); *H04N 13/254* (2018.05); *H04N 2213/001* (2013.01)

(58) Field of Classification Search
CPC .... H04N 13/271; A61B 1/00193; A61B 1/05; A61B 1/00009; A61B 1/00096; A61B 1/00097; A61B 1/00194; A61B 1/0605
See application file for complete search history.

(56) References Cited

U.S. PATENT DOCUMENTS

| | | | |
|---|---|---|---|
| 10,089,737 B2 | 10/2018 | Krieger et al. | |
| 10,143,523 B2 | 12/2018 | Mariampillai et al. | |
| 10,426,345 B2 | 10/2019 | Shekhar et al. | |
| 10,925,465 B2 | 2/2021 | Tully et al. | |
| 10,949,986 B1 | 3/2021 | Colmenares et al. | |
| 2003/0210812 A1 | 11/2003 | Khamene et al. | |
| 2004/0169673 A1 | 9/2004 | Crampe et al. | |
| 2011/0098553 A1 | 4/2011 | Robbins et al. | |
| 2011/0306832 A1* | 12/2011 | Bassan | A61B 1/0008 600/109 |
| 2014/0094655 A1* | 4/2014 | Newman | A61B 1/05 600/109 |
| 2017/0280969 A1* | 10/2017 | Levy | A61B 1/00177 |
| 2017/0280970 A1 | 10/2017 | Sartor et al. | |
| 2018/0184887 A1* | 7/2018 | Abou El Kheir | A61B 1/3132 |
| 2019/0209000 A1* | 7/2019 | Treado | A61B 1/00167 |
| 2019/0231220 A1* | 8/2019 | Refai | A61B 1/051 |
| 2020/0005521 A1 | 1/2020 | Youngquist et al. | |
| 2020/0059640 A1 | 2/2020 | Browd et al. | |
| 2020/0105065 A1 | 4/2020 | Youngquist et al. | |
| 2020/0169649 A1* | 5/2020 | Ouyang | A61B 1/00006 |
| 2020/0195903 A1 | 6/2020 | Komp et al. | |
| 2020/0201022 A1* | 6/2020 | Shameli | A61B 1/0005 |
| 2020/0281454 A1* | 9/2020 | Refai | A61B 1/0676 |
| 2021/0045618 A1 | 2/2021 | Stricko et al. | |
| 2021/0145254 A1 | 5/2021 | Shekhar et al. | |
| 2021/0196385 A1 | 7/2021 | Shelton et al. | |
| 2021/0338060 A1 | 11/2021 | Tully et al. | |

FOREIGN PATENT DOCUMENTS

| | | | | |
|---|---|---|---|---|
| EP | 3102141 B1 | 8/2019 | | |
| KR | 20110038205 A | * | 4/2011 | ......... A61B 1/00181 |
| WO | 2007115825 A1 | 10/2007 | | |
| WO | 2010067267 A1 | 6/2010 | | |
| WO | 2018046091 A1 | 3/2018 | | |

* cited by examiner

ENDOSCOPIC IMAGING SYSTEMS FOR GENERATING THREE DIMENSIONAL IMAGES, AND ASSOCIATED SYSTEMS AND METHODS

CROSS-REFERENCE TO RELATED APPLICATION

This application claims the benefit of U.S. Provisional Patent Application No. 63/082,027, filed Sep. 23, 2020, and titled "ENDOSCOPIC IMAGING SYSTEMS FOR GENERATING THREE DIMENSIONAL IMAGES, AND ASSOCIATED SYSTEMS AND METHODS," which is incorporated herein by reference in its entirety.

TECHNICAL FIELD

The present technology generally relates to endoscopic imaging systems, and more specifically, to endoscopic imaging systems including endoscopes having imaging arrays for generating three-dimensional virtual views of a scene—such as a body cavity of a patient—from multiple perspectives.

BACKGROUND

Medical endoscopes are used to examine internal organs or other features in a body of a patient. Endoscopes can be inserted into the body through a natural body opening or an incision made in the body, and then advanced to a desired point of observation. Typically, endoscopes include optics for capturing light at a distal end thereof and for conveying the light to an observer and/or to an image capture device. For example, some endoscopes are rigid and include relay optics for transmitting the light from the distal end to an image capture device. Other endoscopes are flexible and use fiber optics for transmitting the light. In general, image quality is better using rigid optical architectures. Fiber optics are used in applications where more flexibility is required. The image data is captured by an image sensor at the tip of the endoscope ("chip-in-tip") or transmitted via fiber optics to an image sensor at a proximal end of the endoscope. The latter is often chosen for situations requiring disposable tips.

In general, current endoscopes include only a few camera inputs positioned for optimum image capture based on the desired application (e.g., form of surgery)—most commonly a single camera or fixed stereo pair of cameras. However, such conventional endoscopes suffer from (i) limited field of view, (ii) limited depth of field, and (iii) limited spatial resolution. Also, an operator of such conventional endoscopes cannot adjust the perspective or accurately perceive depth from the scene without physically moving the endoscope within the patient.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Figure 1:
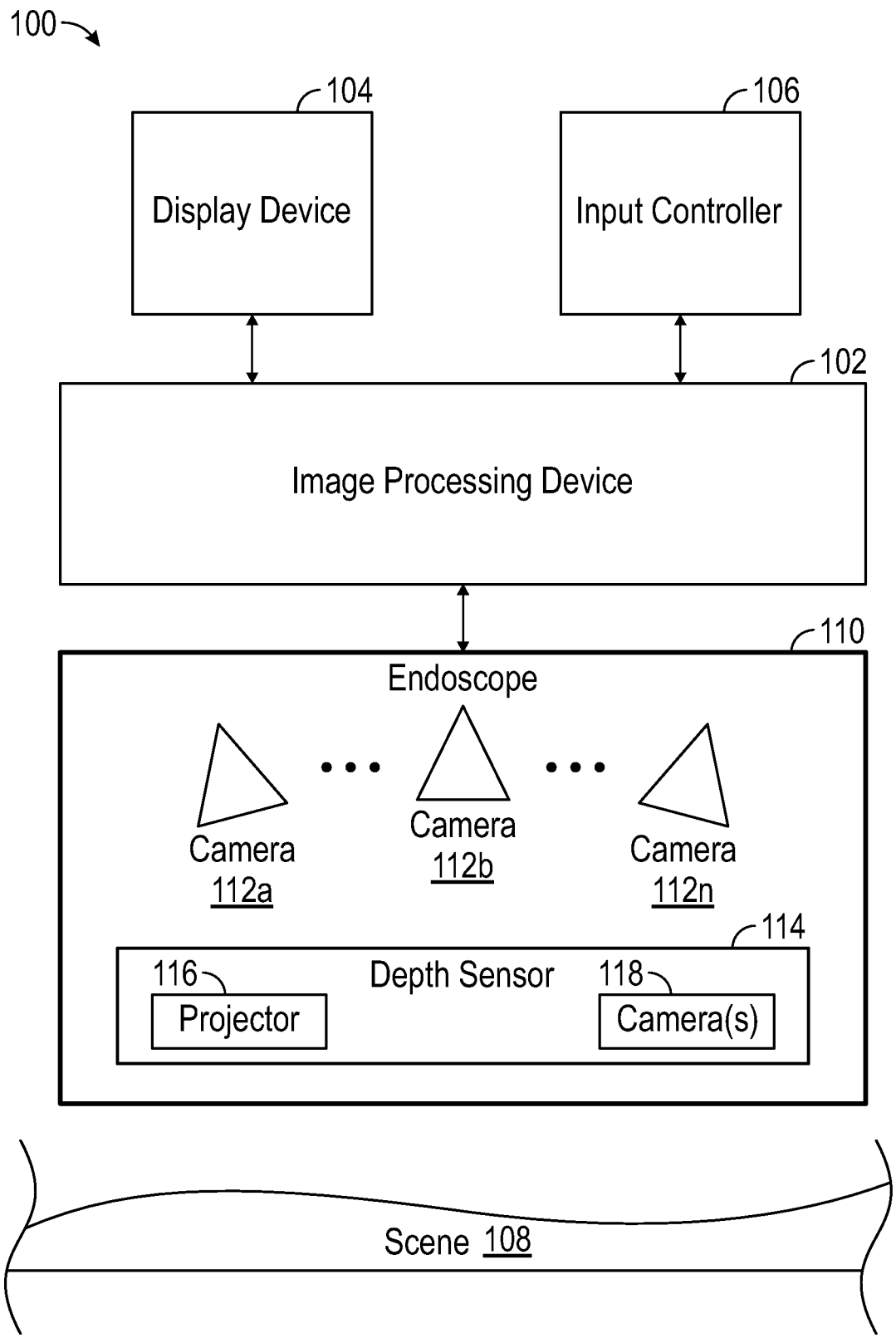
FIG. 1 is a schematic view of an endoscopic imaging system in accordance with embodiments of the present technology.

Aspects of the present disclosure are directed generally to endoscopic imaging systems for capturing three-dimensional (3D) images within a body cavity of a patient, and associated devices and methods. In several of the embodiments described below, for example, an endoscopic imaging system includes a processing device communicatively coupled to (i) an endoscope, (ii) an input controller, and (iii) a display device. The endoscope can include a distal tip having a distal face configured to face a scene, such as a portion of the body cavity of the patient. The endoscope can further include a plurality of first cameras configured to capture first image data of the scene, a projector configured to project a structured light pattern into the scene, and one or more second cameras configured to capture second image data of the scene including the structured light pattern. In some embodiments, the first cameras are RGB and/or plenoptic cameras configured to capture light in the visible spectrum and the second cameras are infrared cameras configured to capture light in the infrared spectrum.

The image processing device can receive the first and second image data in real-time or near real-time and process the image data to generate a 3D image of the scene at the perspective of a virtual camera. The 3D image can be output to the display device to be viewed by a user of the system. In some aspects of the present technology, the image processing device can process the first and second image data to vary the perspective, the aperture, the focus plane, and/or another parameter of the virtual camera without requiring the endoscope to be physically moved within the patient. In some embodiments, for example, the user can operate the input controller to control the position and orientation of the virtual camera.

Specific details of several embodiments of the present technology are described herein with reference to FIGS. 1-6G. The present technology, however, can be practiced without some of these specific details. In some instances, well-known structures and techniques often associated with endoscopes, camera arrays, light field cameras, image reconstruction, depth sensors, etc., have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

The headings provided herein are for convenience only and should not be construed as limiting the subject matter disclosed.

I. Selected Embodiments of Endoscopic Imaging Systems

FIG. 1 is a schematic view of an endoscopic imaging system 100 ("system 100") in accordance with embodiments of the present technology. In the illustrated embodiment, the system 100 includes an image processing device 102 that is operably/communicatively coupled to one or more display devices 104, one or more input controllers 106, and an endoscope 110. In other embodiments, the system 100 can comprise additional, fewer, or different components. In some embodiments, the system 100 can include some features that are generally similar or identical to those of the mediated-reality imaging systems disclosed in (i) U.S. patent application Ser. No. 16/586,375, titled "CAMERA ARRAY FOR A MEDIATED-REALITY SYSTEM," and filed Sep. 27, 2019 and/or (ii) U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," filed May 12, 2020, each of which is incorporated herein by reference in its entirety.

In the illustrated embodiment, the endoscope 110 includes one or more cameras 112 (identified individually as cameras 112a-112n; which can also be referred to as first cameras 112) that are each configured to capture first image data of a scene 108 from a different perspective. The scene 108 can be, for example, a region of an organ or other structure within a body cavity of a patient. As described in greater detail below with reference to FIGS. 2A-6G, the endoscope 110 can include a rigid or flexible elongate body, and the cameras 112 can be positioned at a distal portion of the body. In some embodiments, the cameras 112 are positioned at fixed locations and orientations relative to one another. For example, the cameras 112 can be structurally secured to/in the distal portion of the endoscope 110 at predefined fixed locations and orientations. In some embodiments, the cameras 112 can be positioned such that neighboring ones of the cameras 112 share overlapping views of the scene 108. In some embodiments, the cameras 112 in the endoscope 110 are synchronized to capture images of the scene 108 substantially simultaneously (e.g., within a threshold temporal error).

In some embodiments, all or a subset of the cameras 112 can be light-field/plenoptic cameras that are configured to capture information about the light field emanating from the scene 108 (e.g., information about the intensity of light rays in the scene 108 and also information about a direction the light rays are traveling through space). Therefore, in some embodiments the images captured by the cameras 112 can encode depth information representing a surface geometry of the scene 108. In some embodiments, all or a subset of the cameras 112 can be RGB cameras, hyperspectral cameras, and/or other types of cameras. In some embodiments, the cameras 112 are substantially identical. In other embodiments, the cameras 112 can include multiple cameras of different types. For example, different subsets of the cameras 112 can have different intrinsic parameters such as focal length, sensor type, optical components, and the like. The cameras 112 can have charge-coupled device (CCD) and/or complementary metal-oxide semiconductor (CMOS) image sensors and associated optics. Such optics can include a variety of configurations including lensed or bare individual image sensors in combination with larger macrolenses, microlens arrays, prisms, and/or negative lenses. For example, the cameras 112 can be separate light-field cameras each having their own image sensors and optics. In other embodiments, some or all of the cameras 112 can comprise separate microlenslets (e.g., lenslets, lenses, microlenses) of a microlens array (MLA) that share a common image sensor.

In the illustrated embodiment, the endoscope 110 further includes a depth sensor 114. In some embodiments, the depth sensor 114 includes (i) one or more projectors 116 configured to project a structured light pattern onto/into the scene 108 and (ii) one or more depth cameras 118 (which can also be referred to as second cameras) configured to capture second image data of the scene 108 including the structured light projected onto the scene 108 by the projector 116. The projector 116 and the depth cameras 118 can operate in the same wavelength and, in some embodiments, can operate in a wavelength different than the cameras 112. For example, the cameras 112 can capture the first image data in the visible spectrum, while the depth cameras 118 capture the second image data in the infrared spectrum. In some embodiments, the depth cameras 118 have a resolution that is less than a resolution of the cameras 112. For example, the depth cameras 118 can have a resolution that is less than 70%, 60%, 50%, 40%, 30%, or 20% of the resolution of the cameras 112. In other embodiments, the depth sensor 114 can include other types of dedicated depth detection hardware (e.g., a LiDAR detector) for determining the surface geometry of the scene 108. In other embodiments, the endoscope 110 can omit the projector 116 and/or the depth cameras 118.

In some embodiments, the image processing device 102 is configured to (i) receive the first image data captured by the cameras 112 (e.g., light-field images, light field image data, RGB images, hyperspectral images) and depth information from the depth sensor 114 (e.g., the second image data captured by the depth cameras 118), and (ii) process the image data and depth information to synthesize (e.g., generate, reconstruct, render) a three-dimensional (3D) output image of the scene 108 corresponding to a virtual camera perspective. The output image can correspond to an approximation of an image of the scene 108 that would be captured by a camera placed at an arbitrary position and orientation corresponding to the virtual camera perspective. In some embodiments, the image processing device 102 is further configured to receive or store calibration data for the cameras 112 and/or the depth cameras 118 and to synthesize the output image based on the image data, the depth information, and/or the calibration data. More specifically, the depth information and calibration data can be used/combined with the images from the cameras 112 to synthesize the output image as a 3D (or stereoscopic 2D) rendering of the scene 108 as viewed from the virtual camera perspective. In some embodiments, the image processing device 102 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," which is incorporated herein by reference in its entirety. In other embodiments, the image processing device 102 is configured to generate the virtual camera perspective based only on the images captured by the cameras 112—without utilizing depth information from the depth sensor 114. For example, the image processing device 102 can generate the virtual camera perspective by interpolating between the different images captured by one or more of the cameras 112 (e.g., as described in detail below with reference to FIG. 5).

The image processing device 102 can synthesize the output image from image data captured by a subset (e.g., two or more) of the cameras 112 in the endoscope 110, and does not necessarily utilize images from all of the cameras 112. For example, for a given virtual camera perspective, the image processing device 102 can select a stereoscopic pair of images from two of the cameras 112 that are positioned and oriented to most closely match the virtual camera perspective. In some embodiments, the image processing device 102 (and/or the depth sensor 114) is configured to estimate a depth for each surface point of the scene 108 relative to a common origin and to generate a point cloud and/or 3D mesh that represents the surface geometry of the scene 108. For example, in some embodiments the depth cameras 118 of the depth sensor 114 can detect the structured light projected onto the scene 108 by the projector 116 to estimate depth information of the scene 108. In some embodiments, the image processing device 102 can estimate depth from multiview image data from the cameras 112 using techniques such as light field correspondence, stereo block matching, photometric symmetry, correspondence, defocus, block matching, texture-assisted block matching, structured light, and the like, with or without utilizing information collected by the depth sensor 114. In other embodiments, depth may be acquired by a specialized set of the cameras 112 performing the aforementioned methods in another wavelength.

In some embodiments, functions attributed to the image processing device 102 can be practically implemented by two or more physical devices. For example, in some embodiments a synchronization controller (not shown) controls images displayed by the projector 116 and sends synchronization signals to the cameras 112 to ensure synchronization between the cameras 112 and the projector 116 to enable fast, multi-frame, multi-camera structured light scans. Additionally, such a synchronization controller can operate as a parameter server that stores hardware specific configurations such as parameters of the structured light scan, camera settings, and camera calibration data specific to the camera configuration of the endoscope 110. The synchronization controller can be implemented in a separate physical device from a display controller that controls the display device 104, or the devices can be integrated together.

The image processing device 102 can comprise a processor and a non-transitory computer-readable storage medium that stores instructions that, when executed by the processor, carry out the functions attributed to the image processing device 102 as described herein. Although not required, aspects and embodiments of the present technology can be described in the general context of computer-executable instructions, such as routines executed by a general-purpose computer, e.g., a server or personal computer. The present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The invention can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the invention described below can be stored or distributed on computer-readable media, including magnetic and optically readable and removable computer discs, stored as in chips (e.g., EEPROM or flash memory chips). Alternatively, aspects of the invention can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the invention.

The virtual camera perspective can be controlled by an input controller 106 that provides a control input corresponding to the location and orientation of the virtual camera perspective. The output images corresponding to the virtual camera perspective can be outputted to the display device 104. In some embodiments, the image processing device 102 can vary the perspective, the depth of field (e.g., aperture), the focus plane, and/or another parameter of the virtual camera (e.g., based on an input from the input controller) to generate different 3D output images without physically moving the endoscope 110. The display device 104 is configured to receive output images (e.g., the synthesized three-dimensional rendering of the scene 108) and to display the output images for viewing by one or more viewers. In some embodiments, the image processing device 102 can receive and process inputs from the input controller 106 and process the captured images from the endoscope 110 to generate output images corresponding to the virtual perspective in substantially real-time as perceived by a viewer of the display device 104 (e.g., at least as fast as the frame rate of the endoscope 110).

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. The virtual camera perspective can then be derived to correspond to the position and orientation of the head-mounted display device 104 such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller, etc.) that enables a viewer to manually control the virtual perspective displayed by the display device 104.

II. Selected Embodiments of Endoscopes

Figure 2A:
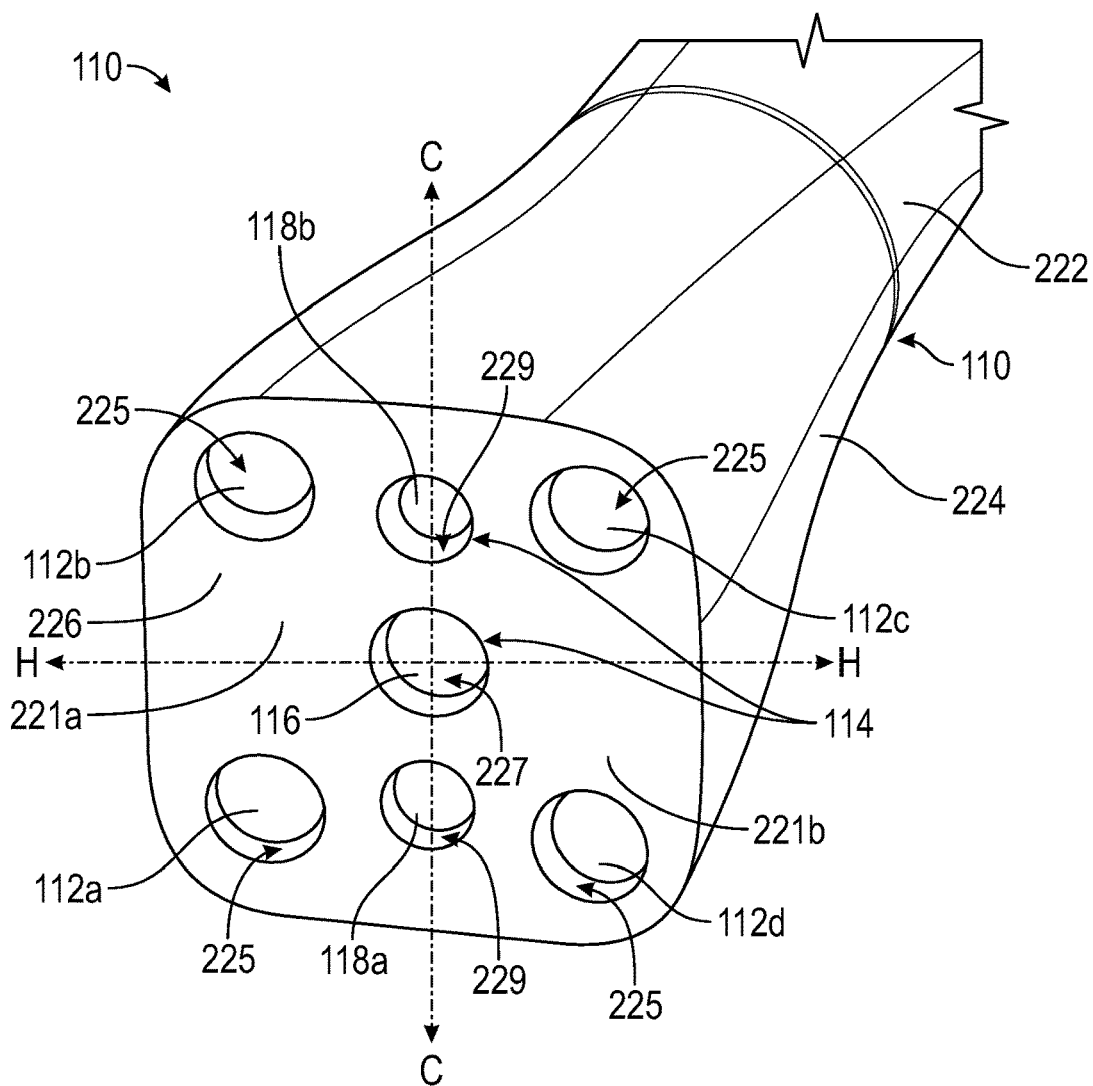
FIG. 2A is an enlarged perspective front view of a distal portion of the endoscope of FIG. 1 in accordance with embodiments of the present technology.

FIG. 2A is an enlarged perspective front (proximally-facing) view of a distal portion or region of the endoscope 110 of FIG. 1 in accordance with embodiments of the present technology. In the illustrated embodiment, the endoscope 110 includes (i) an elongated body 222 and (ii) a distal tip 224 coupled to or integrally formed with the elongated body 222 and having a distal face 226. The distal face 226 is configured to face the scene 108 (FIG. 1). The endoscope 110 is configured (e.g., shaped, sized) to be inserted through a natural opening or an incision in a body of a patient and advanced to a desired point of observation. The elongated body 222 can be flexible or rigid and can be made from metal, plastic, composite, and/or other materials. In some embodiments, the elongated body 222 is formed from a lubricious material (e.g., polytetrafluoroethylene (PTFE)) or has a lubricious outer layer to facilitate its advancement through the body of the patient. The elongated body 222 can include several lumens including fiber optic lumens, fluid lumens, working lumens (e.g., for tools), etc. In some embodiments, the distal tip 224 is removable from the elongated body 222 for cleaning or replacement thereof. For example, the distal tip 224 can be disposable. In some embodiments, the elongated body 222 can have a diameter of between about 5-15 millimeters (e.g., between about 8-9 millimeters), and the distal tip 224 can have a greater diameter of between about 10-20 millimeters (e.g., between about 10-12 millimeters).

In the illustrated embodiment, the distal face 226 of the endoscope 110 has a generally square perimeter with a curved (e.g., concave) surface. In other embodiments, the distal face 226 can have other shapes (e.g., planar, rectilinear, circular, rectangular, polygonal, irregular). In some embodiments, the distal face 226 can have rounded corners to, for example, facilitate insertion and advancement of the endoscope 110 through a patient. The cameras 112 (identified individually as first through fourth cameras 112a-112d, respectively) and the depth sensor 114—including the projector 116 and a pair of the depth cameras 118 (identified individually as a first depth camera 118a and a second depth camera 118b)—are positioned at the distal face 226 and have fields of view that extend distally from the distal face 226. As used herein, a camera or other optical component being "positioned at the distal face" means that the camera or other component can send or receive light at distal face. For example, the cameras 112 can each have a lens or lenslet at the distal face 226 that receives light from the scene 108 (FIG. 1) and passes the light to an optical channel (e.g., optical fiber, rod lens, or other optical path) coupled to one or more image sensors (e.g., CCD and/or CMOS image sensors). The length of the optical channel and the position of the image sensors can be varied. For example, the optical channels can extend proximally to image sensors positioned at a proximal portion of or even outside the endoscope 110 (e.g., as shown in FIG. 6G), or the image sensors can be positioned within the endoscope and electrically coupled to the image processing device 102 (FIG. 1) and/or other circuitry outside the endoscope 110 (e.g., as shown in FIG. 6F). Accordingly, the cameras 112 and the depth sensor 114 can each be communicatively coupled to the image processing device 102 and/or other components of the system 100 via (i) optical fibers, electrical cables or wires, and/or other routing components (obscured in FIG. 2A) extending through the elongated body 222 and/or (ii) via one or more wireless communication paths.

In some embodiments, the distal face 226 includes a plurality of first openings 225 configured (e.g., shaped, positioned) to align with corresponding ones of the cameras 112, a second opening 227 configured to align with the projector 116, and a plurality of third openings 229 configured to align with corresponding ones of the depth cameras 118 of the depth sensor 114. In some embodiments, some or all the openings 225, 227, 229 can be covered with transparent panels (e.g., glass or plastic, panels) to inhibit the ingress of bodily fluids or other contaminants into the endoscope 110. In some embodiments, the distal face 226 is configured (e.g., shaped) such that the transparent panels across each of the openings 225, 227, 229 are arranged perpendicular to the angle of the cameras 112 and the depth sensor 114 to, for example, reduce distortion in the capture data resulting from reflection, diffraction, and/or scattering of light passing through the panels. In other embodiments, various optical components (e.g., lenses) of the cameras 112 and the depth sensor 114 can project into and/or through the openings 225, 227, 229 in the distal face 226. For example, the optical components of the cameras 112 and the depth sensor 114 can be positioned to sealingly engage the distal face 226.

The depth sensor 114 can be positioned along a central (e.g., radially-inward) portion of the distal face 226 and can be generally aligned along a central axis C of the distal face 226. In some embodiments, the projector 116 is positioned at or proximate a center of the distal face 226 to, for example, ensure that the scene 108 (FIG. 1) is adequately illuminated by the projector 116 for depth estimation during operation. The cameras 112 can be distributed about the distal face 226 radially outward from the depth sensor 114. In the illustrated embodiment, the cameras 112 are positioned symmetrically/equally about the distal face 226 proximate to a perimeter of the distal face 226. For example, each of the cameras 112 can be positioned in a respective corner of the distal face 226 and equally spaced apart from (i) the central axis C and (ii) a horizontal axis H extending perpendicular to the central axis C.

In some aspects of the present technology, the spacing of the cameras 112 and the depth sensor 114 can simplify the processing performed by the image processing device 102 (FIG. 1) when synthesizing the output image corresponding to the virtual camera perspective of the scene 108, as described in detail above. In additional aspects of the present technology, the arrangement of the cameras 112 (e.g., positioned near the perimeter of the distal face 226) generally maximizes the disparity of the cameras 112, thereby improving their imaging resolution. Moreover, because the distal tip 224 is wider than the elongated body 222, the distal tip 224 provides a relatively greater baseline that can increase a depth of field captured by the cameras 112. In other embodiments, the endoscope 110 can include more or fewer of the cameras 112, and/or the cameras 112 can be arranged differently about the distal face 226.

In the illustrated embodiment, the distal face 226 includes (i) a first open portion 221a between the first and second cameras 112a, b in a direction parallel to the central axis C and (ii) a second open portion 221b between the third and fourth cameras 112c, d in the direction parallel to the central axis C. In some embodiments, the first open portion 221a and/or the second open portion 221b provide space for additional tools, pathways, channels, and the like (not shown) to be positioned at the distal face 226 in addition to the cameras 112 and the depth sensor 114 (e.g., in addition to the hardware for generating a 3D visualization of a scene around the endoscope 110). For example, one or more channels that terminate at openings in the first and second portions 221a, b of the distal tip 224 can be aligned with corresponding lumens that extend through the elongated body 222 to permit fluids to be injected into or aspirated from the body of the patient. In some embodiments, one or more surgical tools (e.g., probes, cutting devices, gripping devices) can be mounted at or delivered through channels at the first open portion 221a and/or the second open portion 221b. The surgical tools can be passive, or controlled by one or more devices (e.g., controllers) external to the patient and communicatively coupled to the surgical tools via leads extending through the endoscope 110 and/or via one or more wireless communication paths. In some embodiments, a light source (e.g., an optical fiber) can be positioned at the first open portion 221a and/or the second open portion 221b for illuminating a surgical scene around the distal tip 224. The optical fiber can extend through the endoscope 110 and can operate in the same spectrum as the cameras 112 and/or the depth sensor 114. In yet further embodiments, optics for tracking tools (e.g., surgical tools) can be positioned at the first open portion 221a and/or the second open portion 221b. The tracking optics can include imaging devices, such as infrared (IR) cameras that are each configured to capture images of the scene around the distal tip 224 from a different perspective compared to other ones of the imaging devices. Accordingly, the tracking imaging devices and the cameras 112 can have different spectral sensitives (e.g., infrared vs. visible wavelength). In some embodiments, the tracking imaging devices are configured to capture image data of a plurality of optical markers (e.g., fiducial markers, marker balls) coupled to various tools used during a surgical procedure on the patient.

Figure 2B:
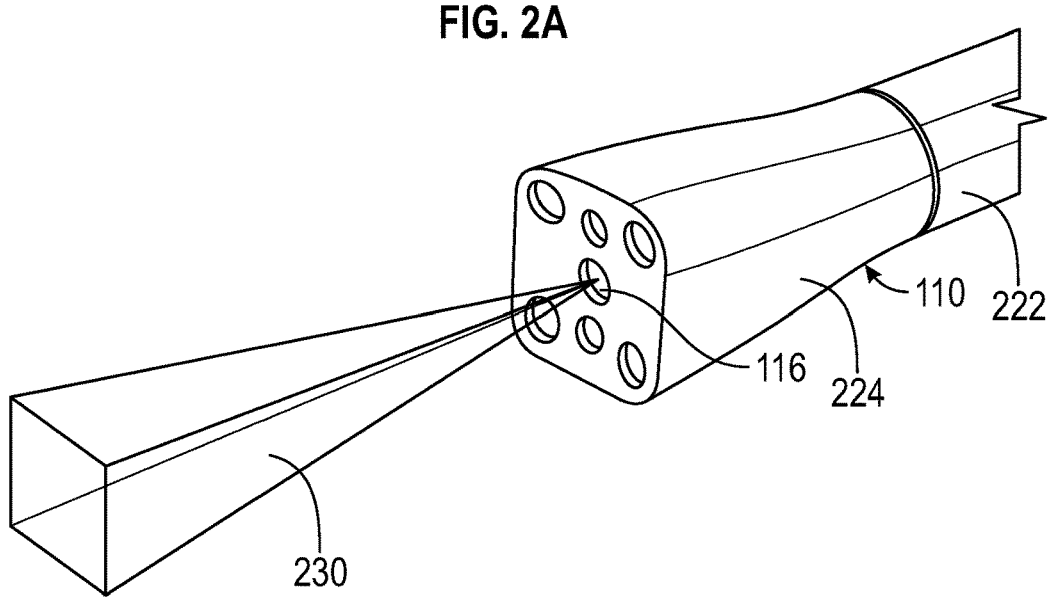
FIG. 2B is an enlarged side perspective view of the endoscope of FIG. 1 illustrating a light pattern emitted by a projector of the endoscope in accordance with embodiments of the present technology.

FIG. 2B is an enlarged side perspective view of the endoscope 110 illustrating a light pattern 230 emitted by the projector 116 in accordance with embodiments of the present technology. In some embodiments, the light pattern 230 comprises a fine pattern of dots or another structured light arrangement. In some embodiments, the projector 116 includes a bundle of multiple optical fibers coupled to a light source such that each of the optical fibers projects one of the dots in the light pattern 230. The light source, such as a laser or light emitting diode (LED), can be positioned within the endoscope 110 (e.g., within the elongated body 222 or the distal tip 224) or can be positioned external to the endoscope 110. The number of optical fibers can be greater than 1,000, greater than 2,000, greater than 5,000, greater than 10,000, greater than 20,000, greater than 40,000, or even higher. In some embodiments, the pattern of dots can be created by selectively enabling different ones (e.g., alternating ones) of the optical fibers in the bundle.

Figure 2C:
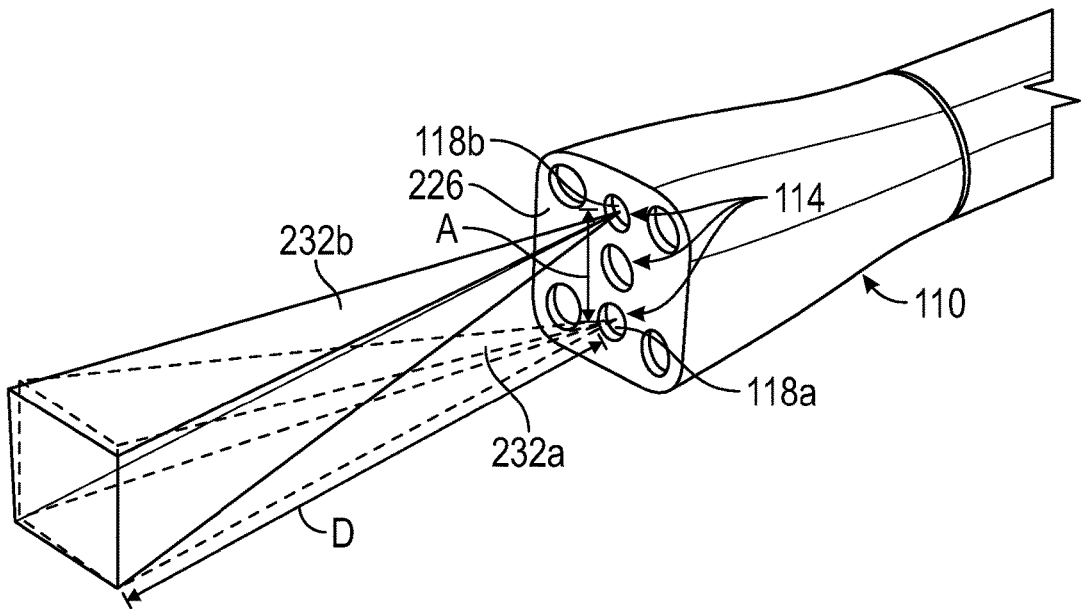
FIG. 2C is an enlarged side perspective view of the endoscope of FIG. 1 illustrating the fields of view of a pair of depth cameras of the endoscope in accordance with embodiments of the present technology.

FIG. 2C is an enlarged side perspective view of the endoscope 110 illustrating a first field of view 232a of the first depth camera 118a and a second field of view 232b of the second depth camera 118b in accordance with embodiments of the present technology. In the illustrated embodiment, the depth cameras 118 are oriented/angled inward toward the center of the distal face 226 (e.g., via the concave shape of the distal face 226) such that the first and second fields of view 232a, b least partially overlap to provide stereoscopic image capture. In some embodiments, a distance A between the depth cameras 118 can be selected to maximize disparity measurements between the depth cameras 118, such as a disparity measurement/estimate using an 8-bit semi-global matching (SGM) algorithm or other suitable computer vision algorithm implemented by the image processing device 102 (FIG. 1). In certain embodiments, the distance A can be less than about 10 millimeters (e.g., about 7 millimeters).

In some embodiments, a portion of the overlapping region of the first and second fields of view 232a, b can correspond to a main focal depth/plane of the depth sensor 114. In some embodiments, the focal depth D of the depth sensor 114 can be selected based on the intended scene 108 (FIG. 1) to be imaged, such as a particular structure or organ within the body of the patient. Accordingly, the configuration of the depth sensor 114 can be selected to ensure accurate depth measurement that facilitates accurate image reconstruction of the scene 108. In some embodiments, the focal depth D of the depth sensor can be between about 5-100 millimeters (e.g., between about 10-40 millimeters) and the depth sensor 114 can provide a depth resolution of between about 10-100 microns (e.g., about 40 microns).

Figure 2D:
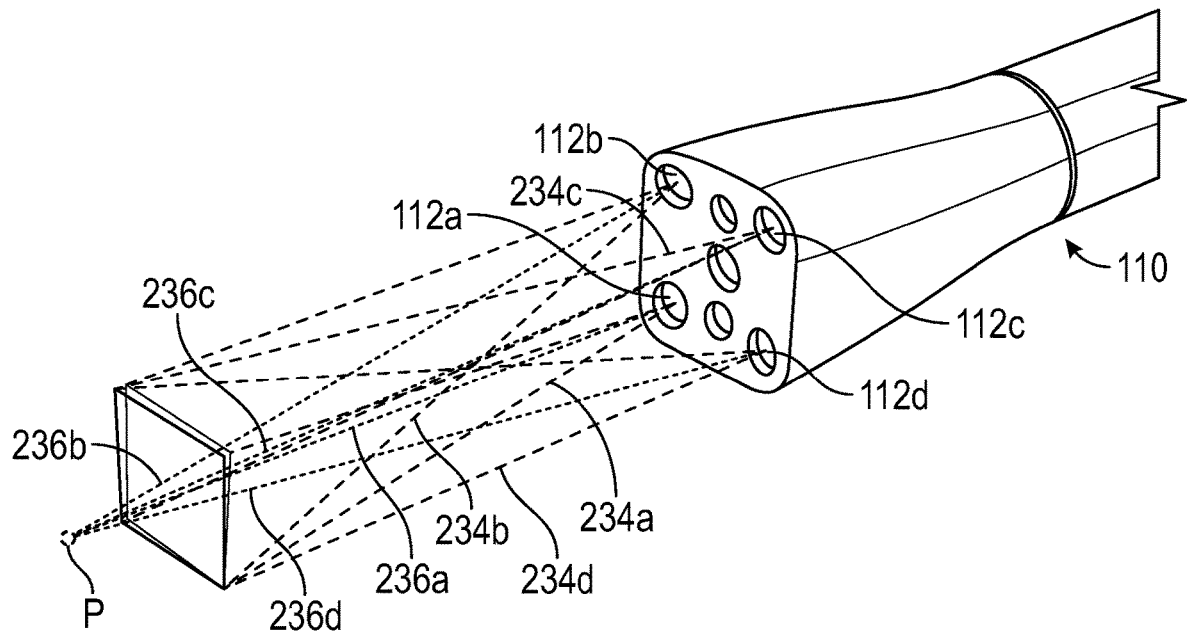
FIG. 2D is an enlarged side perspective view of the endoscope of FIG. 1 illustrating the fields of view of a plurality of cameras of the endoscope in accordance with embodiments of the present technology.

FIG. 2D is an enlarged side perspective view of the endoscope 110 illustrating fields of view 234 (identified individually as first through fourth fields of view 234a-234d, respectively) of the cameras 112 in accordance with embodiments of the present technology. In the illustrated embodiment, the cameras 112 are oriented/angled inward toward the center of the distal face 226 (e.g., via the curved shape of the distal face 226) such that the fields of view 234 at least partially overlap one another to define an imaging volume. In other embodiments, the fields of view 234 of only a subset of the cameras 112 can overlap. As one example, the first field of view 234a of the first camera 112a could partially overlap only one or two of the second through fourth fields of view 234b-234d of the second through fourth cameras 112b-112d, respectively. In some embodiments, the fields of view 234 can be selected (e.g., via selection of an attached lens) to vary the effective spatial resolution of the cameras 112. For example, the fields of view 234 of the cameras 112 can be made smaller to increase their angular spatial resolution and the resulting accuracy of the system 100 (FIG. 1). In some embodiments, the fields of view 234 of the cameras 112 do not fully overlap, but the regions of overlap are tiled such that the resulting imaging volume covered by all the cameras 112 has a selected volume.

In some embodiments, the cameras 112 are identical—for example, having the same focal length, focal depth, resolution, color characteristics, and other intrinsic parameters. In other embodiments, some or all the cameras 112 can be different. For example, the first and second cameras 112a, b (e.g., a first pair of the cameras 112) can have different focal lengths and/or other characteristics than the third and fourth cameras 112c, d (e.g., a second pair of the cameras 112). In some such embodiments, the system 100 (FIG. 1) can render/generate a stereoscopic view independently for each pair of the cameras 112.

Referring to FIGS. 2C and 2D together, each of the cameras 112 can have a focal axis 236 (identified individually as first through fourth focal axes 236a-236b, respectively), and the focal axes 236 can generally converge at a focal point P below the focal depth D of the depth sensor 114. In some aspects of the present technology, the convergence/alignment of the focal axes 236 can generally maximize disparity measurements between the cameras 112. In another aspect of the present technology, the arrangement of the cameras 112 about the distal face 226 of the endoscope provides for high angular resolution of the scene 108 (FIG. 1) that enables the image processing device 102 (FIG. 1) to reconstruct a virtual image of the scene 108.

Referring to FIGS. 1-2D together, the image processing device 102 is configured to receive (i) first image data of the scene 108 from the cameras 112 and (ii) second image data of the scene 108 from the depth cameras 118. The second image data can include encoded depth information based on the pattern of the light projection 230 on the scene 108. The image processing device 102 can then process the first and second image data to reconstruct (e.g., generate, synthesize) a 3D output image of the scene 108 corresponding to a virtual camera perspective. The 3D image of the scene 108 can be displayed on the display device 104 to, for example, a physician, surgeon, nurse, or other user operating the endoscope 110 and/or any additional medical devices associated with a surgical procedure on the patient. The image processing device 102 can generate the output image in real-time or near real-time, and can change the perspective of the output image based on input signals from the input controller 106. In some embodiments, the image processing device 102 can vary the depth of field (e.g., aperture), the focus plane, and/or other parameters of the virtual camera in addition to the perspective.

In some aspects of the present technology, the perspective and/or other parameters of the output image can be changed without changing the physical location or orientation of the distal tip 224 of the endoscope 110. That is, the image processing device 102 can render different perspectives of the scene 108 based only the image data from the cameras 112 and the depth sensor 114 without the user physically moving the endoscope 110 within the body of the patient. In contrast, conventional endoscopes include only a few cameras that, at best, provide a stereoscopic view within a body cavity of a patient. However, the stereoscopic view is not a 3D reconstruction that allows for changes in perspective without moving the endoscope. Accordingly, in some aspects of the present technology the endoscope 110 can increase patient comfort and results by reducing movement of the endoscope 110 during a procedure while also increasing the ability of the user to visualize a target location or observation site within the patient.

Figure 3A:
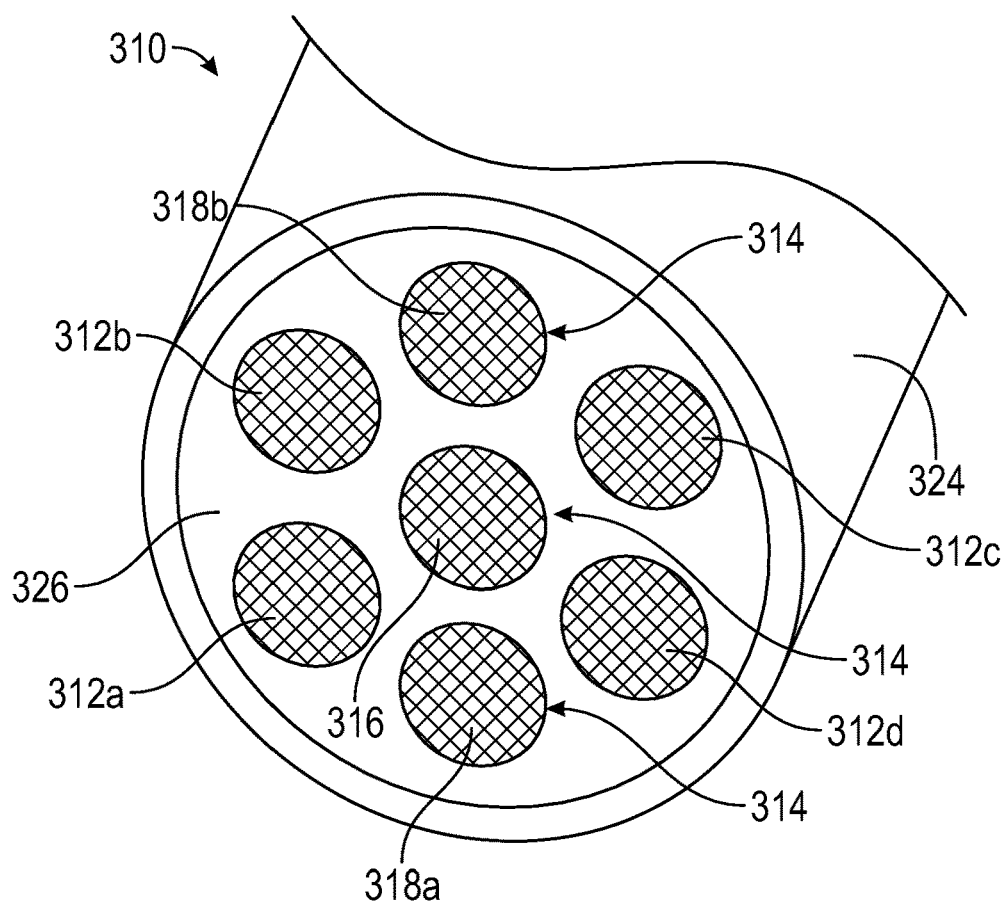
FIG. 3A is an enlarged perspective front view of a distal portion of an endoscope in accordance with additional embodiments of the present technology.

FIG. 3A is an enlarged perspective front (e.g., proximally-facing) view of a distal portion or region of an endoscope 310 in accordance with additional embodiments of the present technology. The endoscope 310 can include some features and/or functions generally similar or identical to those of the endoscope 110 described in detail above with reference to FIGS. 1A-2D, and can be integrated with and/or operated within the system 100 (FIG. 1) in a similar or identical manner as the endoscope 110. In the illustrated embodiment, for example, the endoscope 310 includes a distal tip 324 having a distal face 326. A plurality of cameras 312 (identified individually as first through first cameras 312a-312d, respectively) and a depth sensor 314—including a projector 316 and a pair of depth cameras 318 (identified individually as a first depth camera 318a and a second depth camera 318b)—are positioned at the distal face 326 and have fields of view that extend distally from the distal face 326. The cameras 312 can be plenoptic, RGB, hyperspectral, and/or other types of cameras, and the depth cameras 318 can be infrared cameras and/or other types of cameras (e.g., visible spectrum cameras).

In the illustrated embodiment, the distal face 326 has a generally circular shape and a planar surface, and the depth sensor 314 is positioned along a central axis (e.g., diameter) of the distal face 326. Each of the cameras 312 and the depth cameras 318 can be arranged about the distal face 326 around the projector 316. In some embodiments, the cameras 312 and the depth cameras 318 can be arranged symmetrically about the projector 316 in a circular pattern while, in other embodiments, the cameras 312 and/or the depth cameras 318 can be positioned differently. The cameras 312 can be identical (e.g., having the same focal length, focal depth, resolution, color characteristics, and other intrinsic parameters). In other embodiments, some or all the cameras 312 can be different. For example, the first and second cameras 312a, b (e.g., a first pair of the cameras 312) can have different focal lengths or other characteristics than the third and fourth cameras 312c, d (e.g., a second pair of the cameras 312). Additionally, the distal face 326 can be curved (e.g., convex or concave) to direct the cameras 312 to a desired field of view.

Figure 3B:
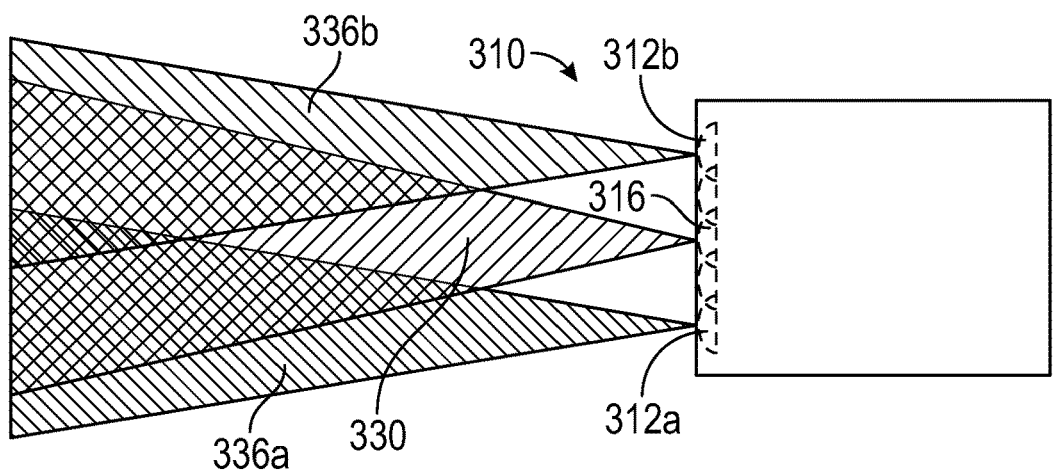
FIG. 3B is an enlarged schematic side view of the endoscope of FIG. 3A illustrating a light pattern emitted by a projector of the endoscope and the fields of view of a plurality of cameras of the endoscope in accordance with embodiments of the present technology.

FIG. 3B is an enlarged schematic side view of the endoscope 310 illustrating a light pattern 330 emitted by the projector 316 and fields of view 334 (identified individually as a first field of view 336a and a second field of view 336b, respectively) of the cameras 312 in accordance with embodiments of the present technology. In the illustrated embodiment, the cameras 312 are configured such that the each of the fields of view 334 at least partially overlap one another to define an imaging volume. In other embodiments, the fields of view 334 of only a subset of the cameras 312 can overlap. Likewise, fields of view of the depth cameras 318 (FIG. 3A; obscured in FIG. 3B) can at least partially overlap one another and the light pattern 330.

Referring to FIGS. 1, 3A, and 3B together, the image processing device 102 is configured to receive (i) image data of the scene 108 from the cameras 312 and (ii) image data from the depth cameras 318 including encoded depth information based on the incidence of the light pattern 330 on the scene 108. The image processing device 102 can then process the images and depth information to generate a 3D output image of the scene 108 corresponding to a virtual camera perspective. In some aspects of the present technology, the image processing device 102 can render output images having different perspectives and/or other parameters of the scene 108 based only the image data from the cameras 312 and the depth sensor 314 without the user physically moving the endoscope 310 within the body of the patient.

Figure 4A:
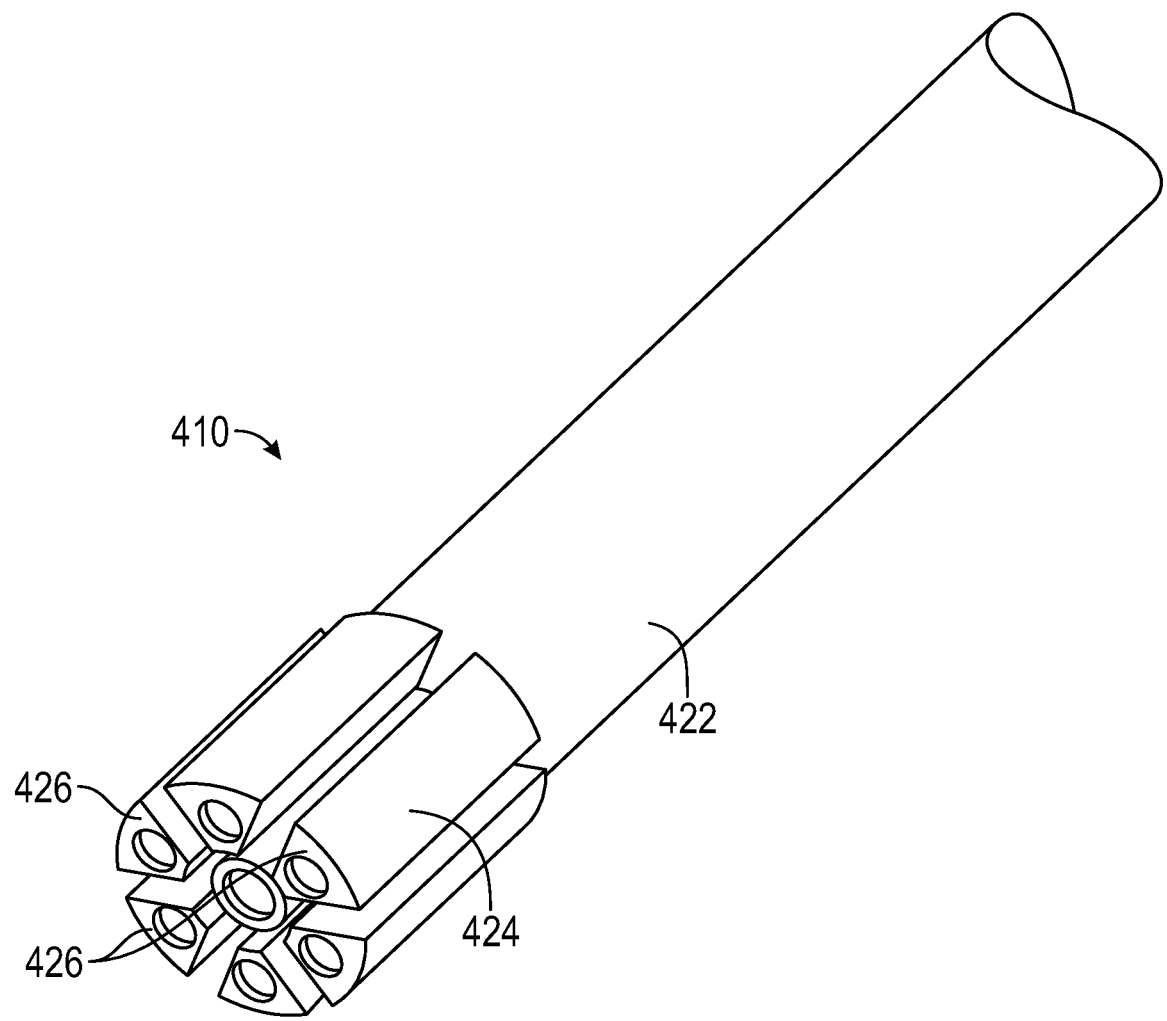
FIGS. 4A and 4B are an enlarged perspective front view and a further enlarged perspective front view, respectively, of a distal portion of an endoscope in accordance with additional embodiments of the present technology.
Figure 4B:
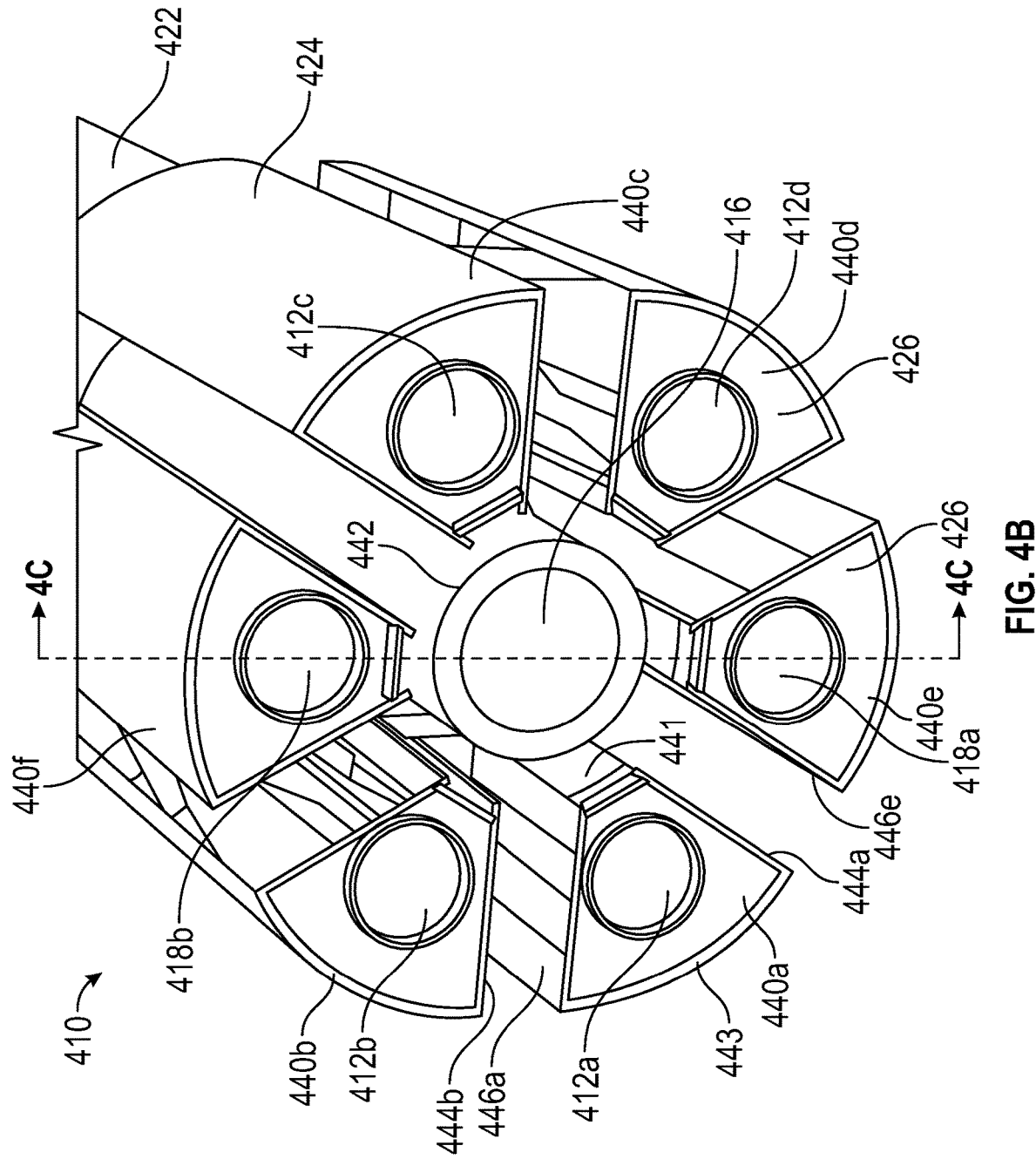

FIGS. 4A and 4B are an enlarged perspective front (e.g., proximally-facing) view and a further enlarged perspective front view, respectively, of a distal portion or region of an endoscope 410 in accordance with additional embodiments of the present technology. The endoscope 410 can include some features and/or functions generally similar or identical to those of the endoscopes 110 and/or 310 described in detail above with reference to FIGS. 1A-3B, and can be integrated with and/or operated within the system 100 (FIG. 1) in a similar or identical manner. Referring to FIGS. 4A and 4B together, for example, the endoscope 410 includes a proximally-extending region 422 and a distal tip 424 having a distal face 426 configured to face the scene 108 (FIG. 1).

Referring to FIG. 4B, however, the distal tip 424 can include a plurality of movable arms 440 (identified as first through sixth arms 440a-440f, respectively) arranged about a central body 442. The arms 440 are movable between (i) a collapsed/compressed position (not shown) in which the arms 440 are positioned radially inward toward/against the central body 442 and (ii) an expanded position shown in FIGS. 4A and 4B in which the arms 440 are positioned radially outward away from the central body 442. In some embodiments, the arms 440 are positioned against the central body 442 in the compressed position such that the distal tip 424 has a minimum cross-sectional dimension (e.g., diameter) for insertion through small body lumens of the patient. In the illustrated embodiment, for example, the arms 440 each have a generally identical wedge-like shape such that adjacent ones of the arms abut one another and the central body 442 in the compressed position.

More specifically, the first arm 440a can include (i) a radially-inward first surface 441, (ii) a radially-outward second surface 443, (iii) a third surface 444a extending outward (e.g., obliquely, at a slant) between the first and second surfaces 441, 443, and (iii) a fourth surface 446a extending outward (e.g., obliquely, at a slant) between the first and second surfaces 441, 443. The other ones of the arms 440 can include similar or identical surfaces/shapes (e.g., a third surface 444b of the second arm 440b and a fourth surface 446e of the fifth arm 440e as shown in FIG. 4B). The first surface 441 is configured (e.g., shaped, positioned, sized) to abut an outer surface of the central body 442 in the compressed position. Similarly, in the compressed position, the third surface 444a is configured to abut the fourth surface 446e of the adjacent fifth arm 440e, and the fourth surface 446a is configured to abut the third surface 444b of the adjacent second arm 440b. In the illustrated expanded position, these surfaces are spaced apart from one another and separated by gaps. The second surfaces 443 of each of the arms 440 can have a curved shaped such that the distal tip 424 and the distal face 426 have a generally circular shape in the compressed position.

The endoscope 410 includes a drive mechanism (not shown) for moving the arms 440 between the compressed and expanded positions. The drive mechanism can include mechanical and/or electrical components for moving the arms 440 such as, for example, one or more hinges, cranks, actuators, gears, levers, movable couplings, and the like. In some embodiments, the drive mechanism can be at least partially positioned outside the endoscope 410 (e.g., proximally outside of the patient during a procedure) and can be actuated by an operator to move the arms 440 between positions. The drive mechanism can move the arms 440 together (e.g., synchronously) and/or move the arms 440 individually relative to one another.

In the illustrated embodiment, the arms 440 each include/contain one of (i) a plurality of cameras 412 (identified individually as first through first cameras 412a-412d, respectively) or (ii) a pair of depth cameras 418. The central body 442 can include a projector 416 that forms a portion of a depth sensor with the depth cameras 418. Accordingly, in the compressed position, the arrangement of the cameras 412, the projector 416, and the depth cameras 418 about the distal face 426 and relative to one another can be generally similar or identical to that of the endoscope 310 described in detail with reference to FIGS. 3A and 3B. However, moving the arms 440 to the expanded position can increase the distance between each of the cameras 412 and the depth cameras 418 relative to the compressed position. For example, a distance between opposing ones of the cameras 412 (e.g., the first camera 412a and the third camera 412c) can be between about 5-10 millimeters (e.g., between about 6-8 millimeters) in the compressed position and between about 10-15 millimeters in the expanded configuration. In some embodiments, only the arms 440 including the cameras 412 can be movable to the expanded configuration. In some embodiments, in the expanded position, the cameras 412 each converge to a plane or point that is just beyond a focal depth of the depth sensor. As described in detail above with reference to FIGS. 1-2D, this can increase the depth resolution of the depth cameras 418.

In some aspects of the present technology, the expanded position provides a greater baseline than the compressed position and, accordingly, the cameras 112 can provide greater angular coverage and range of depth. This can enable the image processing device 102 (FIG. 1) to reconstruct a 3D output image from more perspectives for a given position of the endoscope 410 and/or with greater precision. At the same time, the arms 440 can be moved to the collapsed configuration during, for example, entry into and advancement of the endoscope 310 through the body of the patient. In some aspects of the present technology, this can permit a smaller incision to be made in the patient and/or increase patient comfort and results.

The cameras 412 and/or the depth cameras 418 can comprise a lens or lenslet at the distal face 426 that passes light to an optical channel coupled to an image sensor. To maintain the connectivity of the optical channels when the arms 440 move between the expanded and collapsed positions, in some embodiments the optical channels can be formed from flexible optical fibers that can bend/flex during movement of the arms 440 while maintaining the optical path. In other embodiments, the optical channels can comprise a series of mirrors and/or other optical components configured to maintain optical connections between the lenses and image sensors during movement of the arms 440.

Figure 4C:
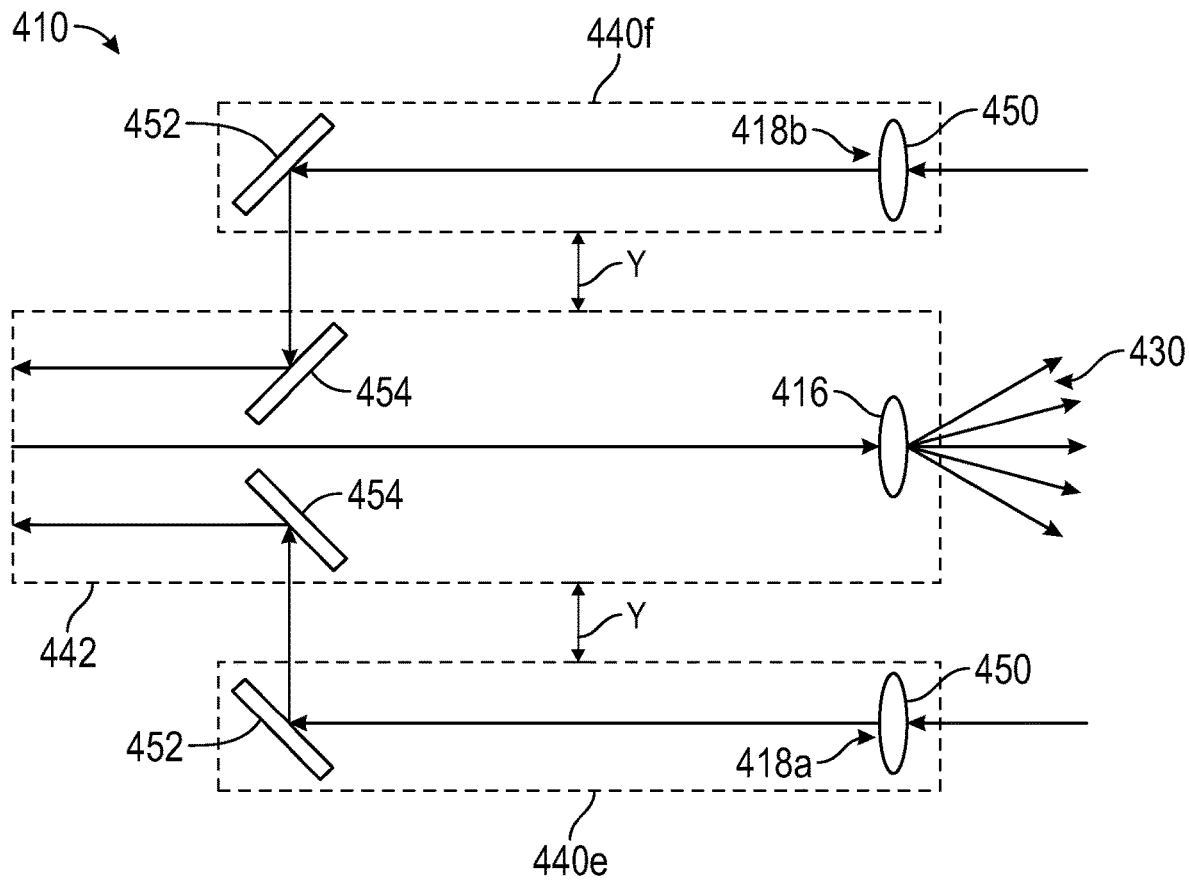
FIG. 4C is a schematic side cross-sectional view of a distal tip of the endoscope of FIGS. 4A and 4B taken along the line 4C in FIG. 4B in accordance with embodiments of the present technology.

For example, FIG. 4C is a schematic side cross-sectional view of the distal tip 424 of the endoscope 410 taken along the line 4C in FIG. 4B in accordance with embodiments of the present technology. In the illustrated embodiment, the arms 440 (e.g., the fifth arm 440e and sixth arm 440f) are in the expanded position away from the central body 442. The depth cameras 418 can each include a lens 450 in the respective one of the arms 440, and an optical path including (i) a first mirror 452 in the respective one of the arms 440 and (ii) a second mirror 454 in the central body 442. In other embodiments, the second mirrors 454 can be positioned in another portion of the endoscope 410 other than arms 440, such as the elongated body 422 (FIGS. 4A and 4B). The optical paths can include one or more optical fibers, rod lenses, waveguides, or the like for routing light between the lenses 450, the first mirrors 452, the second mirrors 454, and the image sensors (not shown).

During operation of the depth cameras 418, each of the lenses 450 receive light (shown schematically by arrows) from the scene 108 (FIG. 1) and direct the light toward the first mirror 452, which directs/reflects the light toward the second mirror 454, which in turn directs the light proximally through the endoscope 410 to, for example, one or image sensors (not shown). In the illustrated embodiment, the arms 440 are each configured to move along an axis Y toward/away from the central body 442 between the compressed and expanded positions. Accordingly, the relative alignment of the first and second mirrors 452, 454 can remain the same or within a threshold tolerance in both the compressed and expanded positions, even while a distance between the first and second mirrors 452, 454 changes. Therefore, the depth cameras 418 can collect and route light along the same optical paths in both the compressed and expanded positions. The cameras 412 (FIG. 4B) can be configured generally similarly or identically. In other embodiments, the endoscope 410 can have other optical paths for routing light therethrough in both the compressed and expanded positions. As further shown in FIG. 4C, light can be routed through the central body 442 (e.g., through a fiber bundle) to the projector 416 for emission as a structured light pattern 430.

Figure 5:
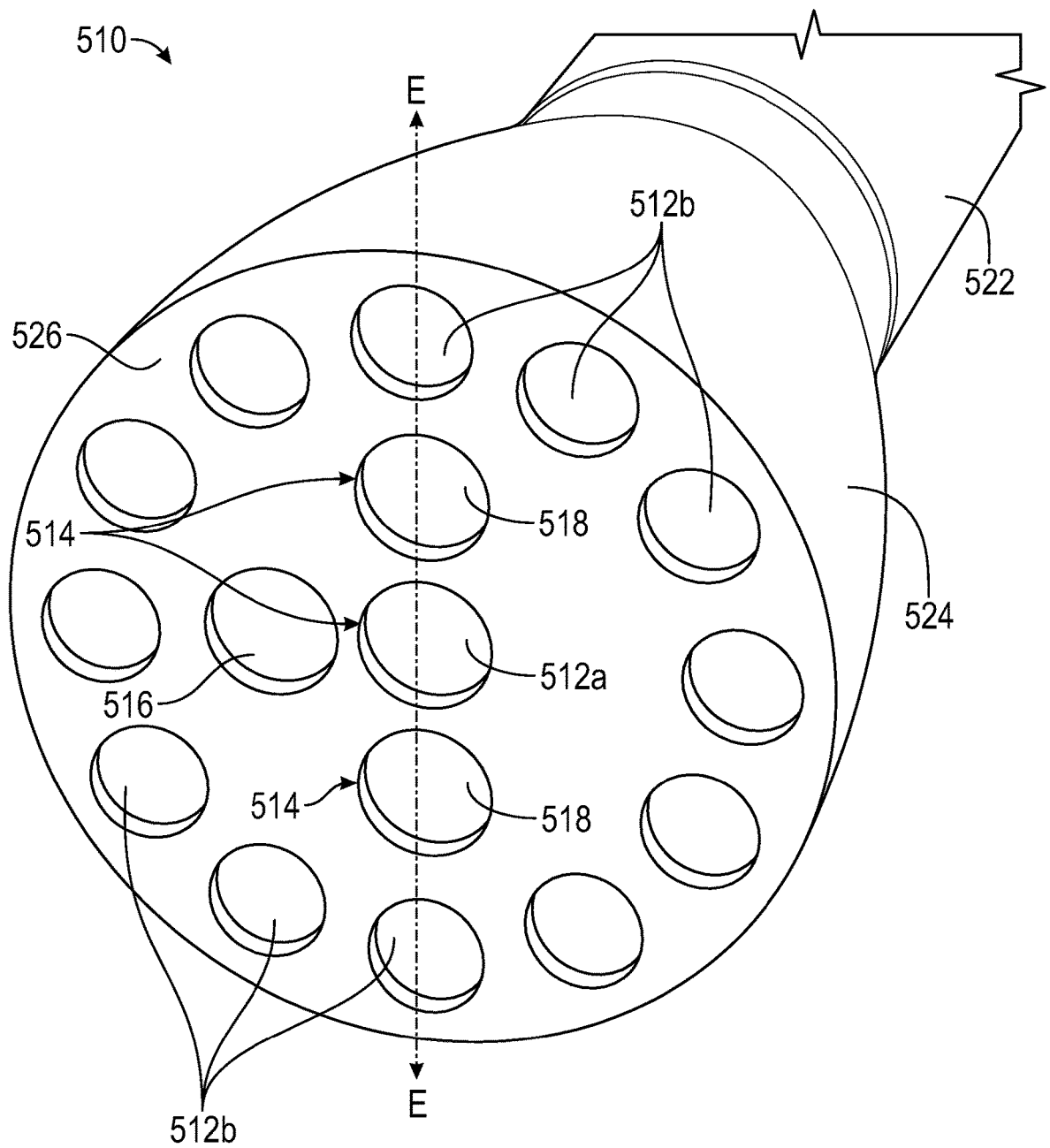
FIG. 5 is an enlarged perspective front view of a distal portion of an endoscope in accordance with additional embodiments of the present technology.

FIG. 5 is an enlarged perspective front (e.g., proximally-facing) view of a distal portion or region of an endoscope 510 in accordance with additional embodiments of the present technology. The endoscope 510 can include some features and/or functions generally similar or identical to those of the endoscopes 110, 310, and/or 410 described in detail above with reference to FIGS. 1A-4C, and can be integrated with and/or operated within the system 100 (FIG. 1) in a similar or identical manner. For example, the endoscope 510 includes a elongated body 522 and a distal tip 524 having a distal face 526. A plurality of cameras 512 (identified individually as a first camera 512a and second cameras 512b) and a depth sensor 514—including a projector 516 and a pair of depth cameras 518—are positioned at the distal face 526 and have fields of view that extend distally from the distal face 526.

In the illustrated embodiment, the distal face 526 has a generally circular shape, and the first camera 512a is positioned at a center of the distal face 526. The second cameras 512b can be positioned around the first camera 512a radially outward of the first camera 512a. In some embodiments, the second cameras 512b are positioned in a ring near a perimeter of the distal face 526. The cameras 512 can all be RGB cameras while, in other embodiments, the cameras 512 can be plenoptic, hyperspectral, and/or other types of cameras. In some embodiments, the first camera 512a has at least one characteristic that is different than the second cameras 512b. For example, the first camera 512a can be larger than, have a greater resolution than, and/or have a wider field of view than the second cameras 512b. In some embodiments, each of the second cameras 512b are identical (e.g., having the same focal length, focal depth, resolution, color characteristics, and other intrinsic parameters). In the illustrated embodiment, the endoscope 510 includes twelve of the second cameras 512b and only one first camera 512a while, in other embodiments, the number and/or arrangement of the cameras 512 can differ. The depth sensor 514 can be positioned at/around the first camera 512a. In the illustrated embodiment, for example, the depth cameras 518 are aligned along a central axis E of the distal face 526 and the projector 516 is offset from the central axis E (e.g., along a longitudinal axis transverse to the central axis E).

Referring to FIGS. 1 and 5 together, the image processing device 102 is configured to receive (i) image data of the scene 108 from the cameras 512 and (ii) image data from the depth cameras 518 including encoded depth information based on a pattern of light projected from the projector 516 onto the scene 108. In some embodiments, the image processing device 102 can then process the images and depth information to generate a 3D output image of the scene 108 corresponding to a selected virtual camera perspective. In other embodiments, the image processing device 102 can process only the image data from the cameras 512—without utilizing the depth information from the depth sensor 514—to generate the 3D output image. In particular, the image processing device 102 can generate the virtual camera perspective by interpolating between the different images captured by the cameras 512. In some aspects of the present technology, the relatively large number of the cameras 512 allows the image processing device 102 to interpolate between images from the different cameras 512 to generate the output image without relying on any measured/calculated depth information. Accordingly, in some embodiments the depth sensor 514 can be omitted entirely, or employed for other purposes such as tool tracking.

Figure 6A:
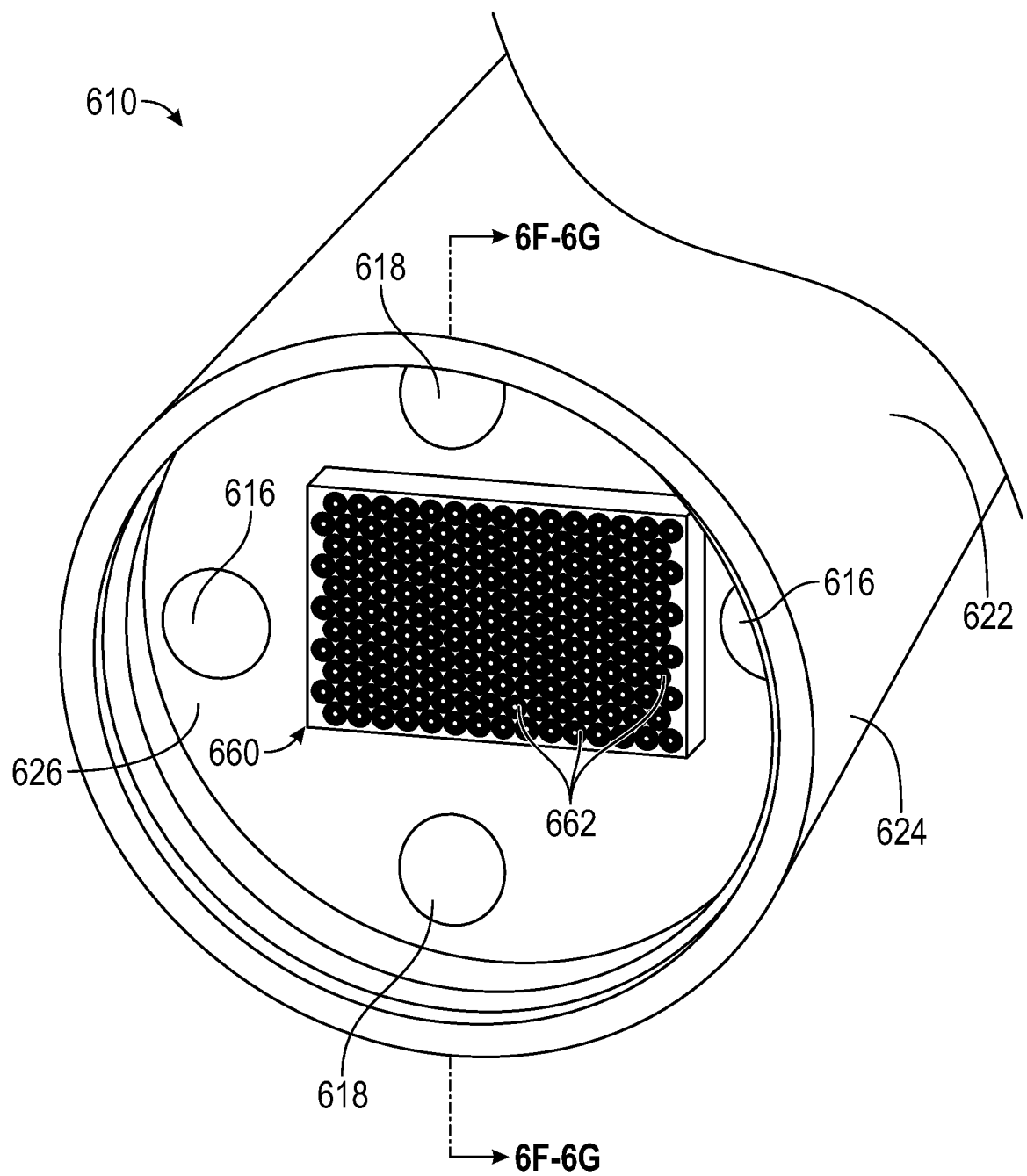
FIGS. 6A and 6B are an enlarged perspective front view and a schematic front view, respectively, of a distal portion of an endoscope in accordance with additional embodiments of the present technology.
Figure 6B:
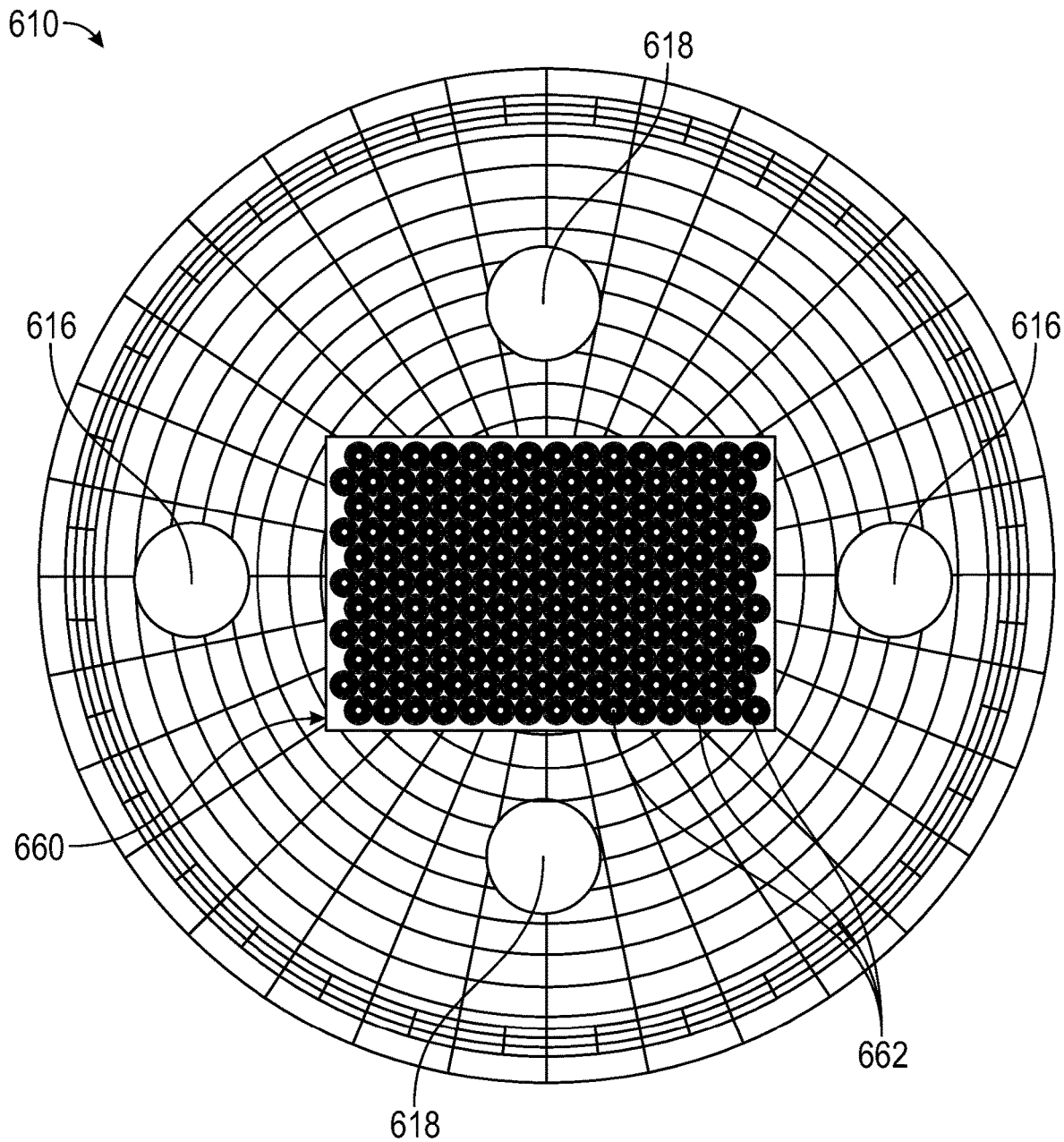

FIGS. 6A and 6B are an enlarged perspective front (e.g., proximally-facing) view and a schematic front view, respectively, of a distal portion or region of an endoscope 610 in accordance with additional embodiments of the present technology. The endoscope 610 can include some features and/or functions generally similar or identical to those of the endoscopes 110, 310, 410, and/or 510 described in detail above with reference to FIGS. 1A-5, and can be integrated with and/or operated within the system 100 (FIG. 1) in a similar or identical manner. Referring to FIG. 6A, for example, the endoscope 610 includes a elongated body 622 and a distal tip 624 having a distal face or objective 626 configured to face the scene 108 (FIG. 1).

Figure 6C:
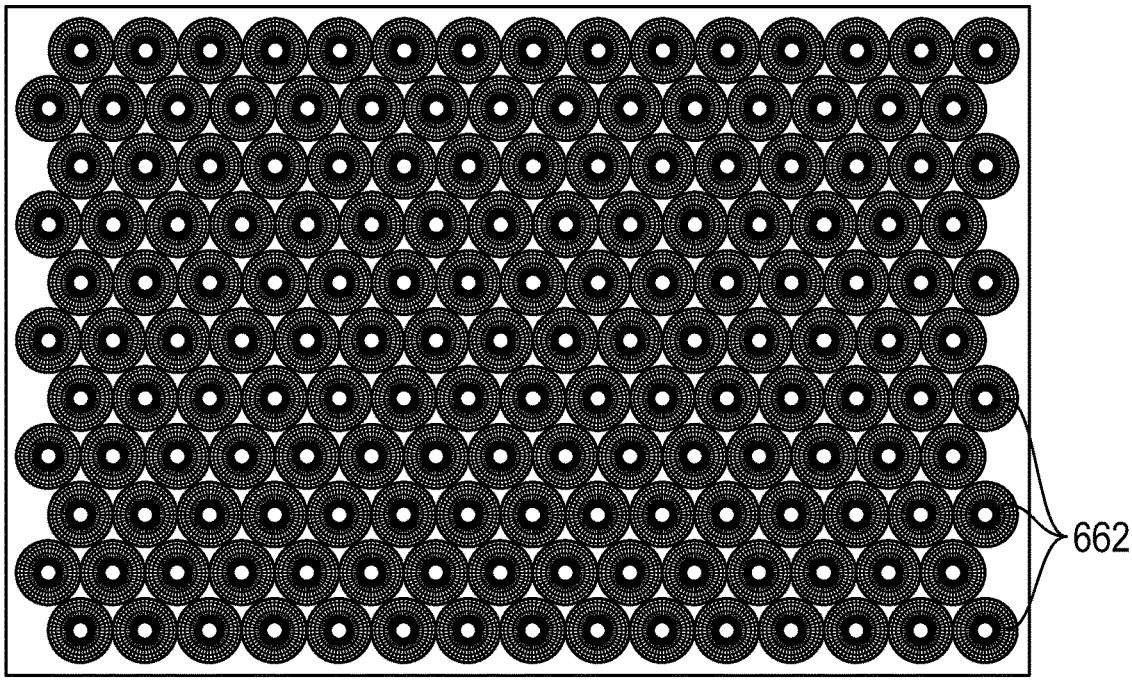
FIGS. 6C-6E are front views of a microlens array (MLA) of the endoscope of FIGS. 6A and 6B illustrating different arrangements of lenslets in the MLA in accordance with embodiments of the present technology.
Figure 6D:
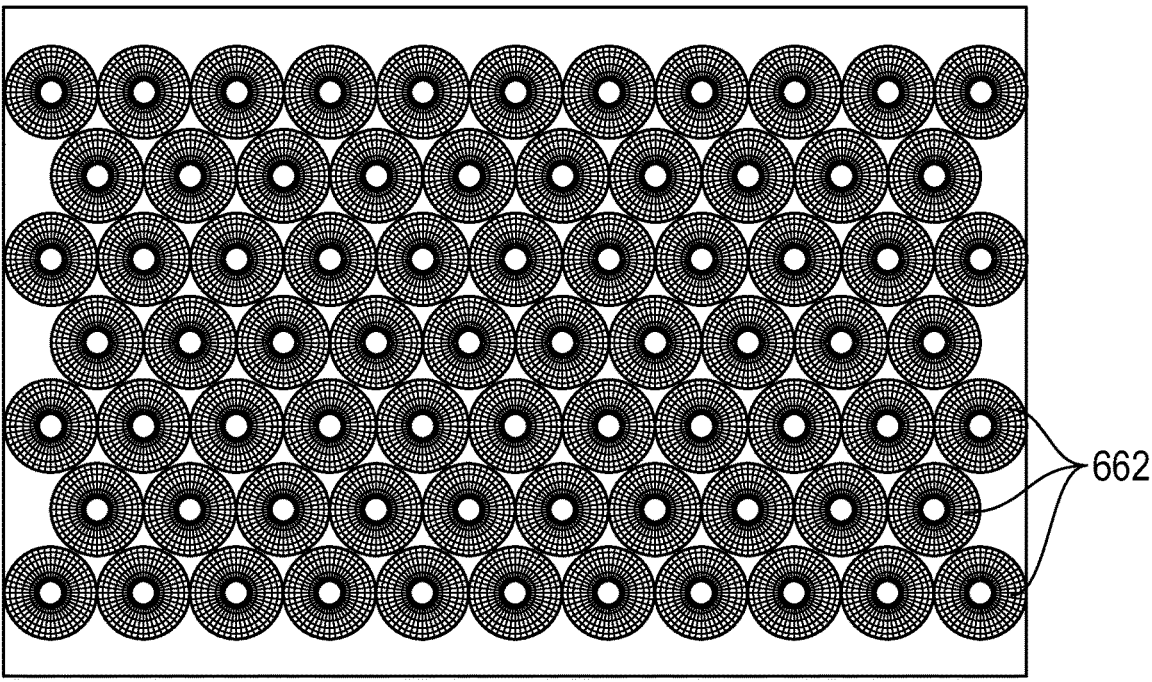
Figure 6E:
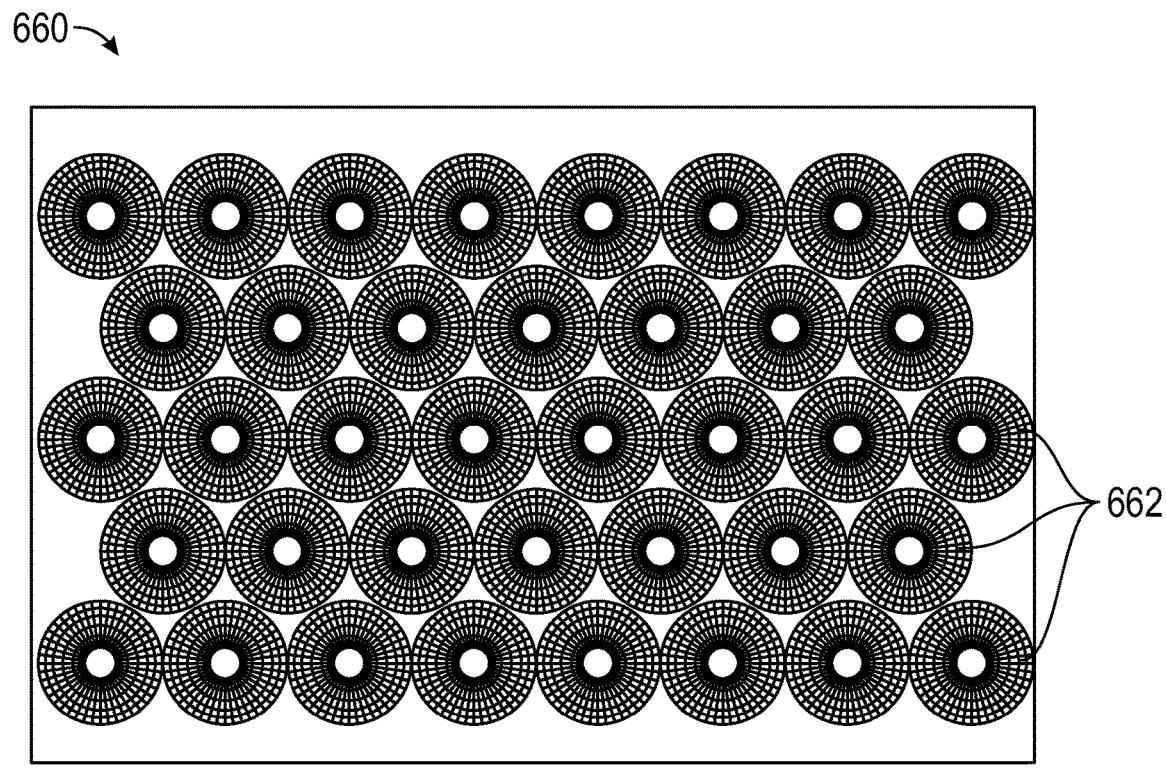
Figure 6F:
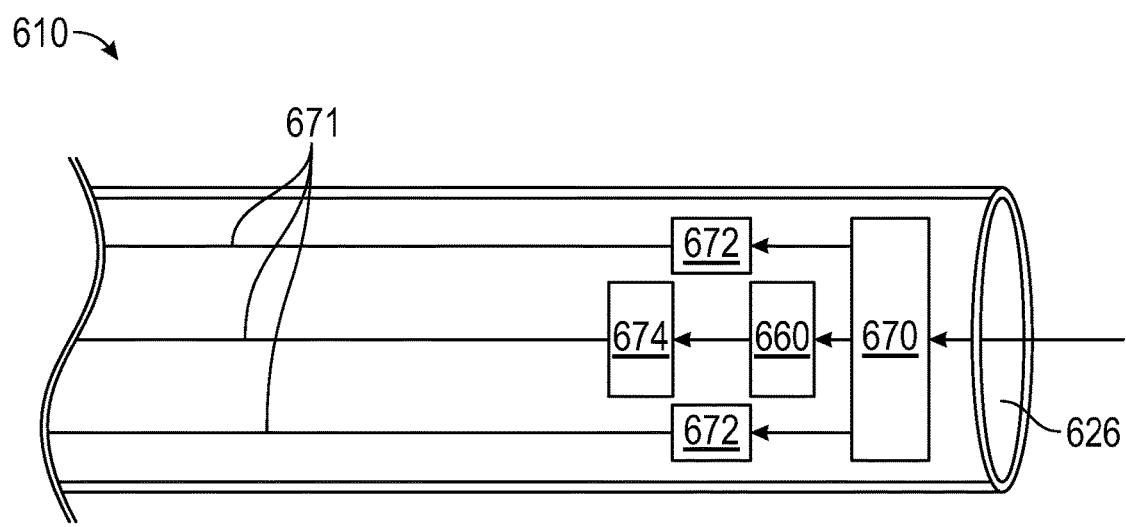
FIG. 6F is a schematic side view of a distal portion of the endoscope of FIGS. 6A and 6B taken along the line 6F-6G in FIG. 6A in accordance with embodiments of the present technology.
Figure 6G:
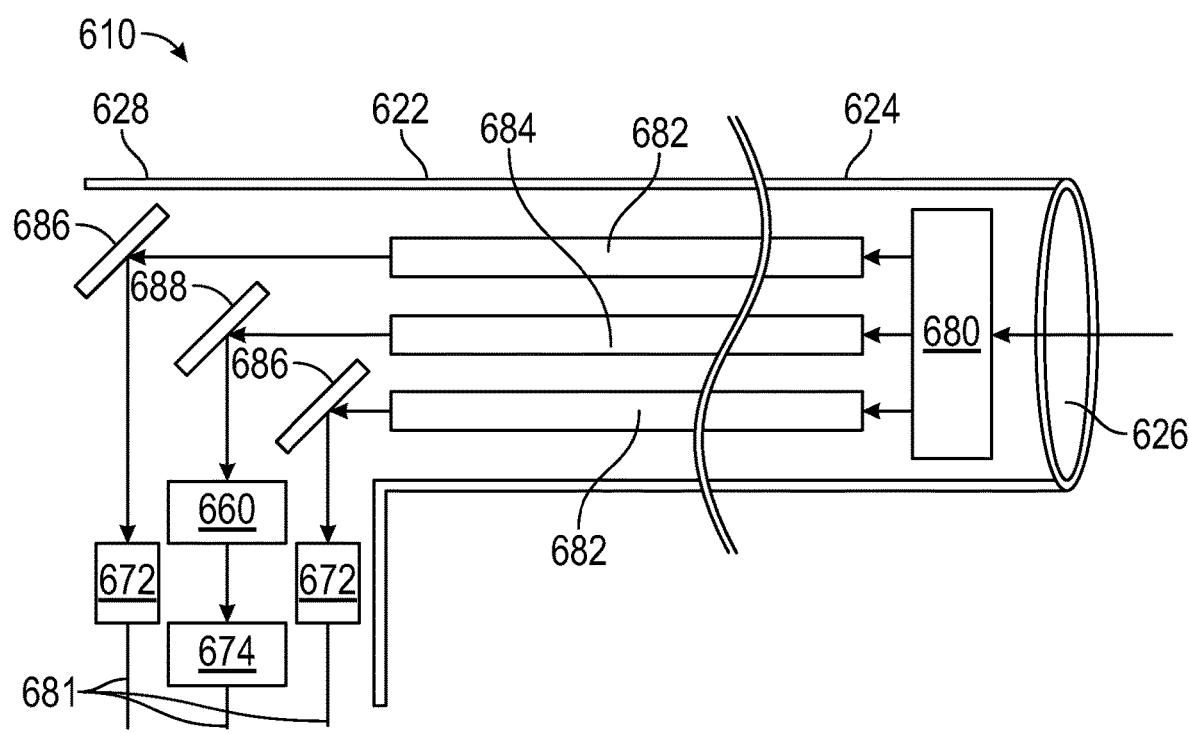
FIG. 6G is a schematic side view of the endoscope of FIGS. 6A and 6B taken along the line 6F-6G in FIG. 6A in accordance with additional embodiments of the present technology.

Referring to FIGS. 6A and 6B together, the distal face 626 includes a microlens array (MLA) 660 including a plurality of microlenses or lenslets 662. The lenslets 662 can each receive light from the scene 108 (FIG. 1) and focus the light on one or more image sensors (e.g., the second image sensor 672 shown in FIGS. 6G and 6F). The size (e.g., diameter) and number of the lenslets 662 can be selected to provide a desired angular and/or spatial resolution based on, for example, the application and intended use of the endoscope 610 (e.g., based on a particular surgical procedure). For example, relatively smaller lenslets 662 can provide for a higher angular resolution at the cost of decreased spatial resolution. FIGS. 6C-6E are front views of the MLA 660 illustrating three different arrangements of the lenslets 662 in the MLA 660 that can provide different spatial and angular resolutions in accordance with embodiments of the present technology. In some embodiments, the arrangement of the lenslets 662 in FIG. 6C can provide a greater angular resolution than the arrangement of the lenslets 662 in FIG. 6D, and the arrangement of the lenslets 662 in FIG. 6D can provide a greater angular resolution than the arrangement of the lenslets 662 in FIG. 6E. Accordingly, the size of the lenslets 662 can be selected to maximize the angular resolution of the MLA 660 based on a required spatial resolution for a particular application.

With additional reference to FIG. 1, a greater angular resolution can enable the image processing device 102 to process image data from the image sensors coupled to the MLA 660 to generate a virtual camera that allows an operator to vary various parameters of the virtual camera, either in live or in post, such as a perspective, depth of field (e.g., aperture), focus plane, and/or other parameter without physically moving the endoscope 610 (e.g., within a body of a patient). For example, the image processing device 102 can quickly interpolate across sub-aperture images from the MLA 660 to generate the virtual camera view. In some embodiments, the endoscope can further include one or more (e.g., a pair) of projectors 616 and one or more (e.g., a pair) of depth cameras 618 positioned at the distal face 626 around the MLA 660. The projectors 616 can emit a structured light pattern, and the depth cameras 618 can capture an image of the scene 108 including the structured light pattern to facilitate depth determination of the scene 108. The image processing device 102 can utilize the depth information to aid in rendering the virtual image of the scene 108. In the illustrated embodiment, the projectors 616 and the depth cameras 618 are positioned symmetrically about the MLA 660 and the distal face 626 while, in other embodiments, the arrangement and/or number of the projectors 616 and the depth cameras 618 can differ.

FIG. 6F is a schematic side view of a distal portion of the endoscope 610 taken along the line 6F-6G in FIG. 6A in accordance with embodiments of the present technology. Referring to FIGS. 6A, 6B, and 6F together, the depth cameras 618 can include first image sensors 672, and the MLA 660 can be optically coupled to a second image sensor 674. The endoscope 610 can further include an optics group 670 having one or more lenses, optical fibers, waveguides, and/or other optical components for (i) receiving light (shown schematically by arrows) through the distal face 626 from the scene 108 (FIG. 1) and (ii) passing the light to the first image sensors 672 and the MLA 660. In turn, the MLA 660 can focus the light of the second image sensor 674. The first and second image sensors 672, 674 can be configured to convert the light to electrical signals, and to route the electrical signals proximally through corresponding wires 671 to the image processing device 102 and/or other components of the system 100 (FIG. 1). Accordingly, in the illustrated embodiment the optical components and the associated image sensors of the depth cameras 618 and the MLA 660 are contained within the distal portion of the endoscope 610 (e.g., at the distal tip 624).

FIG. 6G is a schematic side view of the endoscope 610 taken along the line 6F-6G in FIG. 6A in accordance with additional embodiments of the present technology. Referring to FIGS. 6A, 6B, and 6G together, the endoscope 610 can include (i) an optics group 680, (ii) first optical fibers 682 optically coupled to the optics group 680, (iii) a second optical fiber 684 optically coupled to the optics group 680, (iv) first mirrors 686 optically coupled to corresponding ones of the first optical fibers 682, and (v) a second mirror 688 optically coupled to the second optical fiber 684. In the illustrated embodiment, the optics group 680 is positioned at the distal tip 624 of the endoscope near or at the distal face 626, and the first and second optical fibers 682, 684 extend proximally through the elongated body 622 of the endoscope 610 to the first and second mirrors 686, 688 at a proximal portion 628 of the endoscope 610. The first image sensors 672 of the depth cameras 618 can be optically coupled to the first mirrors 686, and the MLA 660 can be optically coupled to the second mirror 688.

The optics group 680 can include one or more lenses, optical fibers, waveguides, and/or other optical components for receiving light (shown schematically by arrows) through the distal face 626 from the scene 108 (FIG. 1) and passing the light to the first and second optical fibers 682, 684. The first and second optical fibers 682, 684 can route the light to the first and second mirrors 686, 688, respectively, which focus/reflect the light on the first image sensors 672 and the MLA 660, respectively. In turn, the MLA 660 can focus the light of the second image sensor 674. The first and second image sensors 672, 674 can convert the light to electrical signals, and route the electrical signals proximally through corresponding wires 681 to the image processing device 102 and/or other components of the system 100 (FIG. 1). Accordingly, in the illustrated embodiment the optical components and the associated image sensors of the depth cameras 618 and the MLA 660 are distributed throughout the length of the endoscope 610. In some embodiments, the first image sensors 672 and/or the second image sensor 674 can be positioned outside of the endoscope 610.

Referring to FIGS. 6A-6G together, in some embodiments the endoscope 610 can omit the depth cameras 618 and can instead utilize the MLA 660 for imaging a light pattern projected by the projectors 616. For example, the light pattern can be an infrared pattern and an infrared filter can be positioned over a subset of the lenslets 662 of the MLA 660 such that subset of lenslets can detect and image the pattern. In some embodiments, the infrared filter can be selectively toggled over the MLA 660 to provide either infrared image data about the pattern or, for example, visible image data about the scene 108 (FIG. 1).

III. Further Examples

The following examples are illustrative of several embodiments of the present technology:

1. An endoscope, comprising:
   a distal tip having a distal face configured to face a scene;
   a plurality of first cameras configured to capture first image data of the scene;
   a projector configured to project a structured light pattern into the scene; and
   one or more second cameras configured to capture second image data of the scene including the structured light pattern.

2. The endoscope of example 1 wherein the endoscope further includes a proximal region extending from the distal tip, and wherein the distal tip has a cross-sectional dimension greater than a cross-sectional dimension of the proximal region.

3. The endoscope of example 2 wherein the proximal region has a first cross-sectional shape, and wherein the distal tip has a second cross-sectional shape different than the first cross-sectional shape.

4. The endoscope of any one of examples 1-3 wherein the distal face includes a perimeter, and wherein the first cameras are positioned at the distal face proximate to the perimeter.

5. The endoscope of example 4 wherein the projector is positioned at the distal face radially inward of the first cameras.

6. The endoscope of example 5 wherein the projector is positioned at a center of the distal face.

7. The endoscope of any one of examples 1-6 wherein the first image data is in a first spectrum, and wherein the second image data is in a second spectrum different than the first spectrum.

8. The endoscope of any one of examples 1-7 wherein the first image data is in the visible spectrum.

9. The endoscope of example 8 wherein the second image data is in the infrared spectrum.

10. The endoscope of any one of examples 1-9 wherein the first cameras and the second cameras are different types of cameras.

11. The endoscope of any one of examples 1-10 wherein the first cameras are RGB cameras and the second cameras are infrared cameras.

12. The endoscope of any one of examples 1-11 wherein the distal tip includes a plurality of movable arms, and wherein the first cameras and the second cameras are each mounted to a corresponding one of the arms.

13. The endoscope of example 12 wherein the arms are movable from a compressed configuration to an expanded configuration, and wherein the first cameras and the second cameras are positioned farther from one another in the expanded configuration than in the compressed configuration.

14. The endoscope of example 12 or example 13 wherein the arms are movable from a compressed configuration to an expanded configuration, and wherein the arms each have a wedge-like shape such that adjacent ones of the arms abut one another in the compressed configuration.

15. An endoscopic imaging system, comprising:
an endoscope including
a distal tip having a distal face configured to face a scene; and
a plurality of cameras configured to capture image data of the scene from a selected position relative to the scene;
an input controller configured to control a position and orientation of (a) a first virtual perspective of the scene and (b) a second virtual perspective of the scene different from the first virtual perspective;
a processor communicatively coupled to the endoscope and the input controller, wherein the processing device is configured to
generate a first virtual image corresponding to the first virtual perspective based on the image data from the cameras; and
generate a second virtual image corresponding to the second virtual perspective based on the image data from the cameras; and
a display device communicatively coupled to the processing device, wherein the display device is configured to display the first and second virtual images.

16. The endoscopic imaging system of example 15 wherein the processor is configured to generate the first and second virtual images while the endoscope remains at the selected position.

17. The endoscopic imaging system of example 15 or example 16 wherein the processor is configured to generate the first and second virtual images without receiving image data from the cameras with the endoscope positioned at a position other than the selected position.

18. The endoscopic imaging system of any one of examples 15-17 wherein the cameras are first cameras configured to capture first image data of the scene, wherein the endoscope further includes a projector configured to project a structured light pattern into the scene, and wherein the endoscope further includes one or more second cameras configured to capture second image data of the scene including the structured light pattern.

19. The endoscopic imaging system of example 18 wherein the processor is further configured to generate the first and second virtual images based on the second image data.

20. An endoscope, comprising:
a distal tip having a distal face configured to face a scene;
a microlense array positioned at the distal face and including a plurality of lenslets configured to receive first image data of the scene;
at least one projector positioned at the distal face and configured to project a structured light pattern into the scene; and
at least one depth camera positioned at the distal face to capture second image data of the scene including the structured light pattern.

IV. Conclusion

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. An endoscope, comprising:
a distal tip having a distal face configured to face a scene, wherein the distal tip includes a plurality of arms movable from a compressed configuration to an expanded configuration;
a plurality of first cameras of a first type configured to capture first image data of the scene;
a projector configured to project a structured light pattern into the scene; and one or more second cameras of a second type configured to capture second image data of the scene including the structured light pattern, wherein the first type is different than the second type, and wherein
- the first cameras and the second cameras are each mounted to a corresponding one of the arms at the distal face;
- the first cameras and the second cameras are positioned farther from one another in the expanded configuration than in the compressed configuration; and
- the first cameras and the second cameras each have a field of view extending distally from the distal face in the expanded configuration and the compressed configuration.

2. The endoscope of claim 1 wherein the endoscope further includes a proximal region extending from the distal tip, and wherein the distal tip has a cross-sectional dimension greater than a cross-sectional dimension of the proximal region.

3. The endoscope of claim 2 wherein the proximal region has a first cross-sectional shape, and wherein the distal tip has a second cross-sectional shape different than the first cross-sectional shape.

4. The endoscope of claim 1 wherein the distal face includes a perimeter, and wherein the first cameras are positioned at the distal face proximate to the perimeter.

5. The endoscope of claim 4 wherein the projector is positioned at the distal face radially inward of the first cameras.

6. The endoscope of claim 5 wherein the projector is positioned at a center of the distal face.

7. The endoscope of claim 1 wherein the first image data is in a first spectrum, and wherein the second image data is in a second spectrum different than the first spectrum.

8. The endoscope of claim 7 wherein the first image data is in the visible spectrum.

9. The endoscope of claim 8 wherein the second image data is in the infrared spectrum.

10. The endoscope of claim 1 wherein the first cameras of the first type are RGB cameras and the second cameras of the second type are infrared cameras.

11. The endoscope of claim 1 wherein the arms each have a wedge-like shape such that adjacent ones of the arms abut one another in the compressed configuration.

12. The endoscope of claim 1 wherein the plurality of first cameras comprises more than two of the first cameras, and wherein the one or more second cameras comprises at least two of the second cameras.

13. An endoscopic imaging system, comprising:
an endoscope including
- a distal tip having a distal face configured to face a scene, wherein the distal tip includes a plurality of arms movable from a compressed configuration to an expanded configuration; and
- a plurality of cameras mounted to corresponding ones of the arms and configured to capture image data of the scene from a selected position relative to the scene, wherein the cameras comprise at least two different types of cameras, wherein the cameras are positioned farther from one another in the expanded configuration than in the compressed configuration, and wherein the cameras each have a field of view extending distally from the distal face in the expanded configuration and the compressed configuration;
an input controller configured to control a position and orientation of (a) a first virtual perspective of the scene and (b) a second virtual perspective of the scene different from the first virtual perspective;
a processor communicatively coupled to the endoscope and the input controller, wherein the processor is configured to
- generate a first virtual image corresponding to the first virtual perspective based on the image data from the cameras; and
- generate a second virtual image corresponding to the second virtual perspective based on the image data from the cameras; and
a display device communicatively coupled to the processing device, wherein the display device is configured to display the first and second virtual images.

14. The endoscopic imaging system of claim 13 wherein the processor is configured to generate the first and second virtual images while the endoscope remains at the selected position.

15. The endoscopic imaging system of claim 13 wherein the processor is configured to generate the first and second virtual images without receiving image data from the cameras with the endoscope positioned at a position other than the selected position.

16. The endoscopic imaging system of claim 13 wherein the cameras comprise first cameras of a first type configured to capture first image data of the scene and one or more second cameras of a second type different than the first type, wherein the endoscope further includes a projector configured to project a structured light pattern into the scene, and wherein the one or more second cameras are configured to capture second image data of the scene including the structured light pattern.

17. The endoscopic imaging system of claim 16 wherein the processor is further configured to generate the first and second virtual images based on the second image data.

18. An endoscope, comprising:
a longitudinal axis;
a distal tip including a plurality of arm members positioned circumferentially about the longitudinal axis, wherein the arms members are movable from a first position to a second position, and wherein the arm members are positioned farther from the longitudinal axis in the second position than in the first position;
a plurality of first cameras of a first type coupled to corresponding ones of the arm members, wherein the first cameras are configured to capture first image data of the scene;
a projector configured to project a structured light pattern into the scene; and
one or more second cameras of a second type configured to capture second image data of the scene including the structured light pattern, wherein the first type is different than the second type, and wherein the first cameras and the second cameras each have a field of view extending distally from the distal tip in the expanded configuration and the compressed configuration.

19. The endoscope of claim 18 wherein the projector is positioned along the longitudinal axis.

20. The endoscope of claim 18 wherein the arms are movable in a direction orthogonal to the longitudinal axis from the first position to the second position.

* * * * *